(12) United States Patent
Sridhar et al.

(10) Patent No.: US 11,701,046 B2
(45) Date of Patent: Jul. 18, 2023

(54) PORTABLE BRAIN AND VISION DIAGNOSTIC AND THERAPEUTIC SYSTEM

(71) Applicant: Northeastern University, Boston, MA (US)

(72) Inventors: Srinivas Sridhar, Newton, MA (US); Craig Versek, Cranston, RI (US); Peter Bex, Concord, MA (US)

(73) Assignee: Northeastern University, Boston, MA (US)

( * ) Notice: Subject to any disclaimer, the term of this patent is extended or adjusted under 35 U.S.C. 154(b) by 1046 days.

(21) Appl. No.: 16/347,049

(22) PCT Filed: Nov. 2, 2017

(86) PCT No.: PCT/US2017/059803
§ 371 (c)(1),
(2) Date: May 2, 2019

(87) PCT Pub. No.: WO2018/085598
PCT Pub. Date: May 11, 2018

(65) Prior Publication Data
US 2019/0307350 A1   Oct. 10, 2019

Related U.S. Application Data

(60) Provisional application No. 62/416,649, filed on Nov. 2, 2016.

(51) Int. Cl.
*A61B 5/291* (2021.01)
*A61B 5/378* (2021.01)
(Continued)

(52) U.S. Cl.
CPC .............. *A61B 5/291* (2021.01); *A61B 5/378* (2021.01); *A61B 5/4082* (2013.01);
(Continued)

(58) Field of Classification Search
CPC ........ A61B 2562/14; A61B 2562/0209; A61B 5/742; A61B 5/7264; A61B 5/6831;
(Continued)

(56) References Cited

U.S. PATENT DOCUMENTS 10,064,548 B2 * 9/2018 Maddess ................ A61B 5/378
2010/0056935 A1   3/2010 McKinley et al.
(Continued)

FOREIGN PATENT DOCUMENTS

WO   2014025353 A1   2/2014
WO   2014205356 A2  12/2014
(Continued)

OTHER PUBLICATIONS

Jaiswal, N. et al., "Encoding of Visual-Spatial Information in Working Memory Requires More Cerebral Efforts Than Retrieval: Evidence From EEG and Virtual Reality Study", Brain Research, Aug. 6, 2010; vol. 1347: pp. 1-17 doi.org/10.1016/j.brainres.2010.05.086.
(Continued)

*Primary Examiner* — Navin Natnithithadha
(74) *Attorney, Agent, or Firm* — Verrill Dana, LLP

(57) ABSTRACT

A portable wireless neuromonitoring device can be used to diagnose and/or treat conditions of the brain and vision system. The device includes a sensor unit mountable on the head of a human subject and capable of recording signals from the brain in EEG and/or EFEG (electric field encephalography) mode, and the device can be used for simultaneous stimulus display and recording with latency of less than 1 millisecond. The device also includes electrodes that allow rapid set-up and measurement with low impedance contact with the scalp. The device can also be used in conjunction with virtual reality or alternate reality environments.

21 Claims, 15 Drawing Sheets

VR headset with smartphone

NeuroDot Brain Sensor

(51) Int. Cl.
*A61B 3/10* (2006.01)
*A61B 5/00* (2006.01)
*A61B 5/16* (2006.01)

(52) U.S. Cl.
CPC .......... *A61B 5/4088* (2013.01); *A61B 5/6803* (2013.01); *A61B 3/10* (2013.01); *A61B 5/162* (2013.01); *A61B 5/6831* (2013.01); *A61B 5/7264* (2013.01); *A61B 5/742* (2013.01); *A61B 2562/0209* (2013.01); *A61B 2562/14* (2013.01)

(58) Field of Classification Search
CPC ..... A61B 5/162; A61B 5/6803; A61B 5/4088; A61B 5/4082; A61B 5/378; A61B 5/291; A61B 3/10; A61B 5/163
See application file for complete search history.

(56) References Cited

U.S. PATENT DOCUMENTS

| | | |
|---|---|---|
| 2012/0050184 A1 | 3/2012 | Yoo et al. |
| 2016/0081577 A1 | 3/2016 | Sridhar et al. |
| 2016/0081617 A1* | 3/2016 | Iyer ................... A61B 5/6814 600/544 |
| 2016/0113587 A1* | 4/2016 | Kothe ................. A61B 5/7253 600/559 |
| 2016/0235323 A1 | 8/2016 | Tadi et al. |
| 2017/0035317 A1* | 2/2017 | Jung ................... A61B 3/0025 |
| 2017/0188933 A1 | 7/2017 | Huggins et al. |
| 2018/0239430 A1* | 8/2018 | Tadi .................... G06F 3/015 |

FOREIGN PATENT DOCUMENTS

| | | |
|---|---|---|
| WO | 2015161300 A1 | 10/2015 |
| WO | 2016139576 A2 | 9/2016 |

OTHER PUBLICATIONS

Tromp, J. et al., "The combined use of virtual reality and EEG to study language processing in naturalistic environments.", Behavior Research Methods, May 26, 2017, First Online (8 pages) doi: 10.3758/s13428-017-0911-9.

* cited by examiner

PORTABLE BRAIN AND VISION DIAGNOSTIC AND THERAPEUTIC SYSTEM

CROSS REFERENCE TO RELATED APPLICATIONS

This application claims the priority of U.S. Provisional Application No. 62/416,649 filed 2 Nov. 2016 and entitled "Integrated Portable Wireless System for Simultaneous Monitoring in Virtual Reality Environments", the whole of which is hereby incorporated by reference.

STATEMENT REGARDING FEDERALLY SPONSORED RESEARCH OR DEVELOPMENT

The invention was developed with financial support from Grant No. SBIR IIS-1519923 from the National Science Foundation. The U.S. Government has certain rights in the invention.

BACKGROUND

While progress has been made in developing wireless electroencephalography (EEG) platforms [1-7], even the latest commercially available portable systems are challenging to use in less controlled clinical and research settings. Furthermore, EEG measures scalp electric potentials and is a widely used modality for non-invasive brain signal monitoring; however, current EEG measurement techniques have several drawbacks. First, scalp electric potentials are extremely weak (μV range), and are typically overwhelmed by amplifier noise and pick-up noise. With the exception of strong brain rhythms, such as alpha and beta, EEG signals have to be averaged over many repeated trials to average out noise and obtain a usable signal-to-noise ratio (SNR). Second, EEG utilizes a global reference, and without proper compensation, local measurements at high resolution (<0.5 μV/cm) are not feasible. The global reference electrode and the grounding electrode require wiring across the scalp, introducing pick-up noise and making miniaturization impossible. Third, EEG measurements are difficult and time consuming to set up. Liquid electrolytes can lead to conductive bridges, which significantly increase cross-talk between nearby electrodes and further limit EEG's spatial resolution. Dry electrodes tend to be severely noise limited, especially at lower frequencies (Delta and Theta bands). Moreover, many commercially available electrodes do not work well with very thick and curly hair types.

Previous theoretical and computational modelling work [8] suggests that measuring the electric fields generated by neuroelectric activity can provide higher information density (more signals that are less correlated) and better source localization for a given area of scalp coverage. The term "electric field encephalography" (EFEG) describes neuroelectric field based measurement and data processing techniques. US patent application 2012/050184 and WO/2014/025353 disclose implementation details of relevance to EFEG measurement apparatus. Later experimental work [10] addressed the resolution of useful neuroelectric signals at the human scalp using electrode spacing smaller than 2 cm apart—so called "ultra-dense sampling"—demonstrating "strong potential variation at 1 cm scale [that] reflects functional brain activity". Further, WO/2014/205356 discloses implementation details that enable EFEG measurement using ultra-dense sampling.

There remains a need to develop devices, systems, and methods for implementing EFEG in the diagnosis and therapy of brain and other neurological conditions.

SUMMARY

The technology disclosed herein provides a neuromonitoring device and system, as well as a series of methods for using the device or system to diagnose and/or treat conditions of the brain and vision system.

The following are some advantages of the technology: It measures scalp electric potentials (in EEG mode) as well as scalp electric fields (in EFEG mode). The device has a small form factor, and utilizes compact wireless technology, allowing continuous EFEG and EEG measurements without the pickup noise and usability issues created by wired devices. The device performs local measurements of electric fields without the need for an external reference electrode. The device allows simultaneous measurements of global (potential, EEG) and local (electric field, EFEG) brain activity, when using ear-clip reference and active ground electrodes. The device utilizes a biomimetic design related to the ability of some shark species to sense electric fields of prey with high sensitivity. The device features semi-dry scalp electrodes with customized fabrication techniques and materials to reduce artifacts and provide stable long-term signals. The electrodes are designed to work with several hair types, for extended contact periods, and avoid biofouling. The setup time for the device is <2 min. Amplification and digitization of signals are performed close to the sensing location, which reduces movement and electromagnetic interference artifacts. The device offers greater selectivity for neuroelectric signals, which is achieved by utilizing active noise-cancellation through the ground electrode.

One aspect of the present technology is a brain sensing theranostic headset device. The device includes: a sensor unit containing an array of electrodes configured for providing electrical contact between the electrodes and the scalp of a subject wearing the device; a headband upon which the sensor unit is mounted, the headband wearable on the subject's head and adapted for positioning the sensor unit adjacent to a selected brain region; and a display unit capable of displaying visual stimuli to one or both eyes of the subject. The device is capable of measuring signals from the brain of the subject in response to the visual stimuli. The signals include transient and/or steady state visual evoked potentials and fields (VEPF).

Another aspect of the technology is a brain sensing theranostic headset device. The device includes: a sensor unit comprising an array of electrodes configured for providing electrical contact between the electrodes and the scalp of a subject wearing the device; a headband upon which the sensor unit is mounted, the headband wearable on the subject's head and adapted for positioning the sensor unit adjacent to a selected brain region; and a display unit capable of displaying visual stimuli to one or both eyes of the subject. The device is capable of essentially simultaneous display of visual stimuli to the subject and acquisition of brain signals from the subject with a latency of about 1 millisecond or less.

Still another aspect of the technology is a brain sensing theranostic system including either of the headset devices described above and a separate control device in communication with the headset device.

Yet another aspect of the technology is a method of evaluating brain function or vision of a subject. The method includes the following steps: (a) mounting either of the above-described brain sensing theranostic headset devices on the head of a subject, whereby the display unit is oriented to display visual stimuli to the eyes of the subject and the electrodes of the sensor unit are in contact with the subject's scalp which is disposed over a selected brain region; (b) displaying one or more visual stimuli to one or both eyes of the subject using the headset device; (c) measuring signals from the selected brain region of the subject in response to the one or more visual stimuli; and (d) evaluating the subject's brain function or vision based on the measured signals.

Still another aspect of the technology is an electrode for the measurement of electrical signals via low impedance contact with the skin of a subject, such as the scalp. The electrode includes the following components: a base connected to cable extending therefrom for connection to a circuit; an elongated wire loop attached at one end to the base and electrically connected to the cable, the wire loop comprising a metal coated with an electrochemical coating; an elastic tube surrounding the wire loop, the tube sealed at one end to the base and open at the other end; a hydrogel saturated with an electrolyte solution, the hydrogel filling the tube, encasing the wire loop, and protruding from the open end of the tube; and a removable superabsorbent sponge cap covering the open end of the tube, the sponge cap saturated with the electrolyte solution and contacting the protruding hydrogel. The sponge cap is capable of forming an electrical contact with skin. The sponge cap can be removed for resaturation with electrolyte solution, cleaning, or replacement.

Another aspect of the technology is an array of a plurality of electrodes as described above. Each electrode is attached at its base to a curved support frame configured for compressing the electrodes against the skin of a subject, such as the scalp. The shape of the curved support frame is selected so that the electrodes in the array all are aligned roughly perpendicular to and about equally compressed against the skin to form consistent low impedance contacts. The sponge cap is compressible while remaining in good electrical contact, so it compensates for small deviations in the alignment of the array to the subject's head shape. The lengthened narrow construction of the electrodes allows access to the scalp through even fairly thick or curly hair types.

Yet another aspect of the technology is a method of evaluating brain function or vision of a subject. The method includes the steps of: (a) displaying one or more visual stimuli to the subject; and (b) measuring from the subject's brain an EEG and EFEG signal simultaneously in the form of a transient visual evoked potential and field (tVEPF) or a steady state visual evoked potential and field (ssVEPF). In an embodiment of the method, a tVEPF signal is measured by a method including the steps of: (a) displaying a series of repeated visual stimuli to the subject: (b) measuring a series of EEG and EFEG signals, each signal covering an interval extending from about the time of the stimulus to a selected duration after the stimulus; and (c) averaging the series of EEG and EFEG signals to obtain the tVEPF signal. In another embodiment of the method, an ssVEPF signal is measured by a method including the steps of: (a) displaying a series of repeated visual stimuli to the subject: (b) measuring a series of EFEG signals, each signal covering an interval extending from about the time of the stimulus to a selected duration after the stimulus; and (c) computing a spectrum (for example, by averaging windowed Fast Fourier Transforms) that is analyzed in the frequency domain; or (d) computing a spectrogram (for example, by short-time windowed overlapping Fast Fourier Transforms) of the series of EEG and EFEG signals to obtain an ssVEPF signal that is analyzed in both the frequency domain and with variable time resolution. Any of the above methods can be performed for diagnosis, therapy, or combined diagnosis and therapy of a vision or brain condition of the subject. The vision or brain condition can be, for example, selected from the group consisting of neurodegenerative disease, visual impairment, traumatic brain injury, concussion, encephalopathy, multiple sclerosis, glaucoma, dyslexia, dementia, macular degeneration, amblyopia, malingering, optic neuritis, strabismus, convergence insufficiency, color vision anomaly, Alzheimer's disease, Parkinson's disease, Huntington's disease, amyotrophic lateral sclerosis, cerebral ischemia, and stroke.

The technology can also be summarized with the following list of embodiments.

1. A brain sensing theranostic headset device comprising:
   a sensor unit comprising an array of electrodes configured for providing electrical contact between the electrodes and the scalp of a subject wearing the device;
   a headband upon which the sensor unit is mounted, the headband wearable on the subject's head and adapted for positioning the sensor unit adjacent to a selected brain region; and
   a display unit capable of displaying visual stimuli to one or both eyes of the subject; wherein the device is capable of measuring signals from the brain of the subject in response to the visual stimuli, wherein the signals include transient and/or steady state visual evoked potentials and fields (VEPF).

2. The device of embodiment 1, further comprising a control module.

3. The device of embodiment 2, wherein the control module comprises programming that directs (i) presentation of the visual stimuli to a subject wearing the headset device, (ii) acquisition and recording of signals from the subject's brain detected by the sensor unit, and optionally (iii) analysis of the signals.

4. The device of embodiment 3, wherein the program directs presentation of a series of visual stimuli selected to diagnose and/or treat a neurological or visual condition of the subject.

5. The device of any of the previous embodiments, further comprising a wireless transmission module that receives data or instructions for display of the visual stimuli from a remote device and/or that transmits data derived from the measured brain signals to a remote device.

6. The device of any of the previous embodiments, wherein the sensor unit further comprises an amplifier module that receives signals from the electrode array and produces amplified electrode signals and a signal processing module that processes the amplified signals to obtain electric field or electric potential data.

7. The device of embodiment 6, further comprising a wireless transmitter that transmits the data to a control module within the device or to a remote device.

8. The device of embodiment 7, wherein the amplifier module, signal processing module, and wireless transmitter are each located on a separate circuit board within the sensor unit.

9. The device of any of the previous embodiments, wherein the electrode array comprises a reference electrode and an array of sensing electrodes surrounding the reference electrode.

10. The device of any of the previous embodiments, wherein the selected brain region is the visual cortex, and the device is capable of recording transient and/or steady state visual evoked potentials and fields from the visual cortex of the subject in response to visual stimuli delivered through the display unit.

11. The device of any of the previous embodiments, wherein the device is further capable of measuring signals from the brain of the subject by electroencephalography (EEG).

12. The device of embodiment 11, wherein a steady state VEPF measured with the device is at least about four times greater when measured using electric field encephalography (EFEG) than when measured using EEG.

13. The device of any of the previous embodiments, wherein the display unit comprises a mobile device and a mounting structure for the mobile device, the mounting structure attached to the headband, and wherein the mobile device displays the visual stimuli.

14. The device of embodiment 13, wherein the mobile device is programmed to control display of visual stimuli on the mobile device, collect data derived from the measured brain signals, store the data, optionally analyze the data, and transmit data or analyzed data to a remote device.

15. The device of any of the previous embodiments that is capable of operation directed from a remote device.

16. The device of any of the previous embodiments, wherein the display unit comprises virtual reality goggles or an augmented reality system.

17. The device of any of the previous embodiments, wherein the display unit comprises a video screen of a device not attached to the headband.

18. The device of any of the previous embodiments, wherein the display unit is capable of monocular, dichoptic, stereoscopic, binocular, hemifield, multi-focal, static, dynamic, or chromatic image presentation to the subject.

19. The device of any of the previous embodiments, wherein the one or more visual stimuli comprise one or more abstract or realistic objects, one or more scenes, and/or a virtual reality or augmented reality visual environment.

20. The device of any of the previous embodiments that is portable, self-contained, and capable of setup and obtaining data from a human subject in less than about one minute.

21. A brain sensing theranostic headset device comprising:
    a sensor unit comprising an array of electrodes configured for providing electrical contact between the electrodes and the scalp of a subject wearing the device;
    a headband upon which the sensor unit is mounted, the headband wearable on the subject's head and adapted for positioning the sensor unit adjacent to a selected brain region; and
    a display unit capable of displaying visual stimuli to one or both eyes of the subject; wherein the device is capable of essentially simultaneous display of visual stimuli to the subject and acquisition of brain signals from the subject with a latency of about 1 millisecond or less.

22. The device of embodiment 21, wherein the latency is about 1 microsecond or less.

23. The device of embodiment 21 or 22, wherein the display unit comprises a phototransistor coupled to a high gain current-voltage amplifier that provides a digital signal used to trigger data acquisition after presentation of a visual stimulus.

24. The device of any of embodiments 21-23, further comprising a control unit.

25. The device of embodiment 24, wherein the control unit comprises programming that incorporates a stimulus marker into a first frame of an image onset at the onset of a visual stimulus.

26. The device of embodiment 24 or 25, wherein acquired data are time stamped using only one clock or a set of clocks synchronized using Network Time Protocol and compensated to a relative drift of less than 1 millisecond per hour, and wherein the clocks are disposed either in the control unit or in the display unit.

27. The device of any of embodiments 24-26, wherein a mobile device serves as both display unit and control unit.

28. The device of embodiment 27, wherein the sensor unit and mobile device communicate via a USB OTG connection.

29. The device of embodiment 27 or 28, wherein the mobile device serves as a data gateway, communicating with a remote computer or computer network.

30. The device of any of embodiments 21-29, wherein the sensor unit comprises a plurality of electrodes capable of forming a contact impedance of less than 200 kohms with the scalp of a subject wearing the device.

31. The device of embodiment 30, wherein the electrodes are configured for recording brain signals in an EFEG mode.

32. The device of any of embodiments 21-31, wherein the display unit comprises a mobile device and a mounting structure for the mobile device, the mounting structure attached to the headband, and wherein the mobile device displays the visual stimuli.

33. The device of any of embodiments 21-32 that is capable of operation directed from a remote device.

34. The device of any of embodiments 21-33, wherein the display unit comprises virtual reality goggles or an augmented reality system.

35. The device of any of embodiments 21-34, wherein the display unit comprises a video screen of a device not attached to the headband.

36. The device of any of embodiments 21-35, wherein the display unit is capable of dichoptic, binocular, or monocular image presentation to the subject.

37. The device of any of embodiments 21-36 that is portable, self-contained, and capable of setup and obtaining data from a human subject in less than one minute.

38. A brain sensing theranostic system comprising the headset device of any of the previous embodiments and a separate control device in communication with the headset device.

39. The system of embodiment 38, wherein the control module comprises programming that directs (i) presentation of the visual stimuli to a subject wearing the headset device, (ii) acquisition and recording of signals from the subject's brain detected by the sensor unit, and optionally (iii) analysis of the signals.

41. The system of embodiment 39, wherein the programming directs presentation of a series of visual stimuli selected to diagnose and/or treat a neurological or visual condition of the subject.

42. The system of embodiment 39 or 41, wherein the programming provides training of the subject's visual perception.

43. The system of embodiment 39, 41, or 42, wherein the programming supports playing a game or watching a video or a movie.

44. A method of evaluating brain function or vision of a subject, the method comprising:
    (a) mounting the brain sensing theranostic headset device of any of embodiments 1 to 37 on the head of a subject, whereby the display unit is oriented to display visual stimuli to the eyes of the subject and the electrodes of the sensor unit are in contact with the subject's scalp disposed over a selected brain region;
    (b) displaying one or more visual stimuli to one or both eyes of the subject using the headset device;

(c) measuring signals from the selected brain region of the subject in response to the one or more visual stimuli; and (d) evaluating the subject's brain function or vision based on the measured signals.

45. The method of embodiment 44, wherein the subject has or is suspected of having a condition selected from the group consisting of neurodegenerative disease, visual impairment, traumatic brain injury, concussion, encephalopathy, multiple sclerosis, glaucoma, dyslexia, and dementia.

46. The method of embodiment 45, wherein the subject has or is suspected of having a visual impairment selected from the group consisting of macular degeneration, amblyopia, malingering, optic neuritis, strabismus, convergence insufficiency, and color vision anomaly.

47. The method of embodiment 45 or 46, wherein the subject has or is suspected of having a neurodegenerative disease selected from the group consisting of Alzheimer's disease, Parkinson's disease, Huntington's disease, amyotrophic lateral sclerosis, cerebral ischemia, and stroke.

48. The method of any of embodiments 44-47, wherein the step of mounting the device does not include the application of a paste or gel to the scalp of the subject.

49. The method of any of embodiments 44-48, wherein the one or more visual stimuli are presented to the subject in a monocular, dichoptic, stereoscopic, binocular, hemifield, multi-focal, static, dynamic, or chromatic mode.

50. The method of any of embodiments 44-49, wherein a series of visual stimuli are presented to the subject to diagnose, treat, or monitor and simultaneously treat a neurological or visual condition of the subject.

51. The method of any of embodiments 44-50, wherein a series of visual stimuli are presented to the subject to train the subject's visual perception.

52. The method of any of embodiments 44-51, wherein one or more visual stimuli are presented as part of playing a game or watching a video or a movie.

53. The method of any of embodiments 44-52, wherein brain signals are obtained from the subject with the sensor unit operating in EFEG mode or EEG mode.

54. The method of any of embodiments 44-53, which is carried out with the subject in a reclining, sitting, or standing position, or while the subject is in motion.

55. The method of any of embodiments 44-54, wherein the one or more visual stimuli are presented in a virtual reality or augmented reality visual environment.

56. The method of any of embodiments 44-55, wherein the method is carried out in a battlefield, trauma center, field hospital, home, or ambulance setting.

57. The method of any of embodiments 44-56, further comprising video-based eye tracking of the subject.

58. The method of any of embodiments 44-57, wherein the one or more visual stimuli are selected from the group consisting of steady state visual evoked potential or field (ssVEPF), swept contrast VEPF, swept acuity VEPF, motion VEPF, chromatic VEPF, dichoptic VEPF, multichannel VEPF, hemifield VEPF, dark adaptation VEPF, multifocal VEPF, binocular VEPF.

59. The method of embodiment 58, wherein visual acuity is diagnosed and the one or more visual stimuli comprise swept acuity ssVEPF; or wherein vision loss is diagnosed and the one or more visual stimuli comprise multifocal VEPF; or wherein contrast sensitivity function is diagnosed and the one or more visual stimuli comprise swept contrast ssVEPF; or wherein traumatic brain injury is diagnosed and the one or more visual stimuli comprise swept acuity or swept contrast ssVEPF, or multifocal VEPF, or dark adaptation VEPF, of binocular VEPF; or wherein concussion is diagnosed and the one or more visual stimuli comprise swept acuity or swept contrast ssVEPF, or dark adaptation VEPF, of binocular VEPF; or wherein malingering is diagnosed and the one or more visual stimuli comprise swept contrast VEPF or eyetracking; or wherein amblyopia is diagnosed and the one or more visual stimuli comprise swept contrast VEPF; or wherein glaucoma is diagnosed and the one or more visual stimuli comprise multifocal VEPF; or wherein acute macular degeneration is diagnosed and the one or more visual stimuli comprise dark adaptation recovery VEPF; or wherein multiple sclerosis is diagnosed and the one or more visual stimuli comprise swept acuity or swept contrast ssVEPF, or multifocal VEPF; or wherein optic neuritis is diagnosed and the one or more visual stimuli comprise wept acuity or swept contrast ssVEPF, or multifocal VEPF.

60. The method of any of embodiments 44-59, wherein the one or more visual stimuli comprise frequency tagging of an object in an image.

61. An electrode for the measurement of electrical signals via low impedance contact with skin, the electrode comprising:

a base connected to cable extending therefrom for connection to a circuit;

an elongated wire loop attached at one end to the base and electrically connected to the cable, the wire loop comprising a metal coated with an electrochemical coating;

an elastic tube surrounding the wire loop, the tube sealed at one end to the base and open at the other end;

a hydrogel saturated with an electrolyte solution, the hydrogel filling the tube, encasing the wire loop, and protruding from the open end of the tube; and a removable superabsorbent sponge cap covering the open end of the tube, the sponge cap saturated with the electrolyte solution and contacting the protruding hydrogel, wherein the sponge cap is capable of forming an electrical contact with skin.

62. The electrode of embodiment 61, wherein the electrochemical coating comprises Ag and AgCl and has a nano-dendritic structure.

63. The electrode of embodiment 61 or 62, wherein the hydrogel comprises polyvinyl alcohol that has been cross-linked using a freeze-thaw process.

64. The electrode of any of embodiments 61-63, wherein the electrolyte solution comprises a deep eutectic solvent and an aqueous solution of $MgCl_2$ or LiCl.

65. The electrode of embodiment 64, wherein the electrolyte solution further comprises colloidal AgCl and optionally graphene particles in suspension.

66. The electrode of any of embodiments 61-65 having a skin contact impedance of less than 200 kOhm.

67. The electrode of embodiment 66 having a skin contact impedance of less than 100 kOhm.

68. The electrode of any of embodiments 61-67 having a potential drift of about 1 microvolt/second or less in use.

69. The electrode of any of embodiments 61-68 that can be used in contact with bare skin and does not require application of gel or paste to skin.

70. An array of electrodes of any of embodiments 61-69, wherein each electrode is attached at its base to a curved support frame configured for compressing the electrodes against the skin of a subject.

71. The array of embodiment 70 comprising an electrode capable of serving as a reference and a square-shaped array of sensing electrodes surrounding the reference electrode.

72. A method of evaluating brain function or vision of a subject, the method comprising the steps of:

(a) displaying one or more visual stimuli to the subject; and (b) measuring from the subject's brain an EFEG signal in the form of a transient visual evoked potential or stimulus (tVEPF) or a steady state visual evoked potential or stimulus (ssVEPF).

73. The method of embodiment 72, wherein a tVEPF signal is measured by a method comprising the steps of:

(a) displaying a series of repeated visual stimuli to the subject;

(b) measuring a series of EFEG signals, each signal covering an interval extending from about the time of the stimulus to a selected duration after the stimulus; and (c) averaging the series of EFEG signals to obtain a tVEPF signal.

74. The method of embodiment 73, wherein the visual stimuli are repeated at a frequency less than about 5 Hz.

75. The method of embodiment 73 or 74, wherein the visual stimuli comprise a series of flashes.

76. The method of any of embodiments 73-75, wherein the visual stimuli comprise pattern reversal between a pair of images.

77. The method of any of embodiments 73-76, wherein the visual stimuli comprise a scene in which an object of the scene is modulated between stimuli in time, contrast, color, or location.

78. The method of any of embodiments 73-77, wherein steps (a) and (b) are performed simultaneously by a portable, self-contained, wirelessly controlled device.

79. The method of any of embodiments 73-78, wherein the method is performed to assess that status of a vision or brain state of a subject.

80. The method of any of embodiments 73-79, wherein the method is performed for diagnosis, therapy, or combined diagnosis and therapy of a vision or brain condition of the subject.

81. The method of embodiment 80, wherein the vision or brain condition is selected from the group consisting of neurodegenerative disease, visual impairment, traumatic brain injury, concussion, encephalopathy, multiple sclerosis, glaucoma, dyslexia, dementia, macular degeneration, amblyopia, malingering, optic neuritis, strabismus, convergence insufficiency, color vision anomaly, Alzheimer's disease, Parkinson's disease, Huntington's disease, amyotrophic lateral sclerosis, cerebral ischemia, and stroke.

82. The method of embodiment 72, wherein an ssVEPF signal is measured by a method comprising the steps of:

(a) displaying a series of repeated visual stimuli to the subject;

(b) measuring a series of EFEG signals, each signal covering an interval extending from about the time of the stimulus to a selected duration after the stimulus; and (c) performing a fast fourier transform of the series of EFEG signals to obtain an ssVEPF signal.

83. The method of embodiment 82, wherein the visual stimuli are repeated at a frequency greater than about 5 Hz.

84. The method of embodiment 82 or 83, wherein the visual stimuli comprise a series of flashes.

85. The method of any of embodiments 82-84, wherein the visual stimuli comprise pattern reversal between a pair of images.

86. The method of any of embodiments 82-85, wherein the visual stimuli comprise a scene in which an object of the scene is modulated between stimuli in time, contrast, color, or location.

87. The method of any of embodiments 82-86, wherein steps (a) and (b) are performed simultaneously by a portable, self-contained, wirelessly controlled device.

88. The method of any of embodiments 82-87, wherein peaks in the ssVEPF signal are observed at the frequency of the visual stimuli or a harmonic thereof.

89. The method of any of embodiments 82-88, wherein the method is performed to assess that status of a vision or brain state of a subject.

90. The method of any of embodiments 82-89, wherein the method is performed for diagnosis, therapy, or combined diagnosis and therapy of a vision or brain condition of the subject.

91. The method of embodiment 90, wherein the vision or brain condition is selected from the group consisting of neurodegenerative disease, visual impairment, traumatic brain injury, concussion, encephalopathy, multiple sclerosis, glaucoma, dyslexia, dementia, macular degeneration, amblyopia, malingering, optic neuritis, strabismus, convergence insufficiency, color vision anomaly, Alzheimer's disease, Parkinson's disease, Huntington's disease, amyotrophic lateral sclerosis, cerebral ischemia, and stroke.

BRIEF DESCRIPTION OF THE DRAWINGS

FIG. 2C shows an embodiment of a self-contained headset device that uses a cell phone enclosed in a mounting structure as the display unit FIG. 3A schematically depicts an EEFG grade scalp electrode.

FIG. 6A shows the power spectrum and FIG. 6B shows the ratio of eyes closed signal to eyes open signal.

DETAILED DESCRIPTION

Figure 1A:
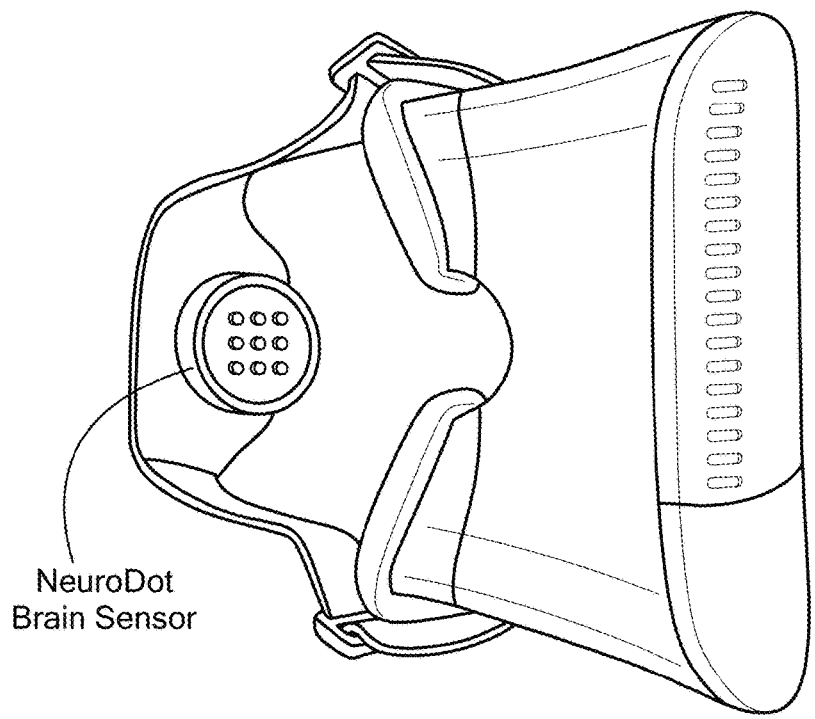
FIG. 1A shows an embodiment of a brain sensing theranostic headset device. The device includes a sensor unit, a headband, and a display unit (a virtual reality headset).
Figure 1B:
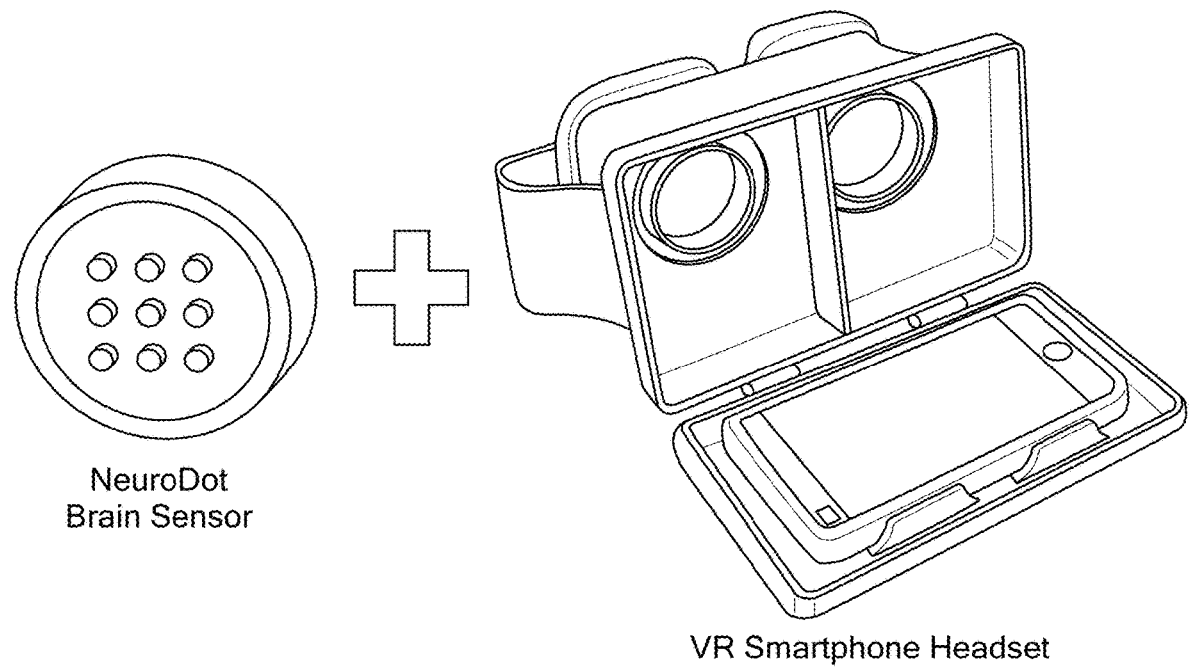
FIG. 1B shows embodiments of a sensor unit (left side) and a display unit (cell phone in a headset mount).
Figure 2A:
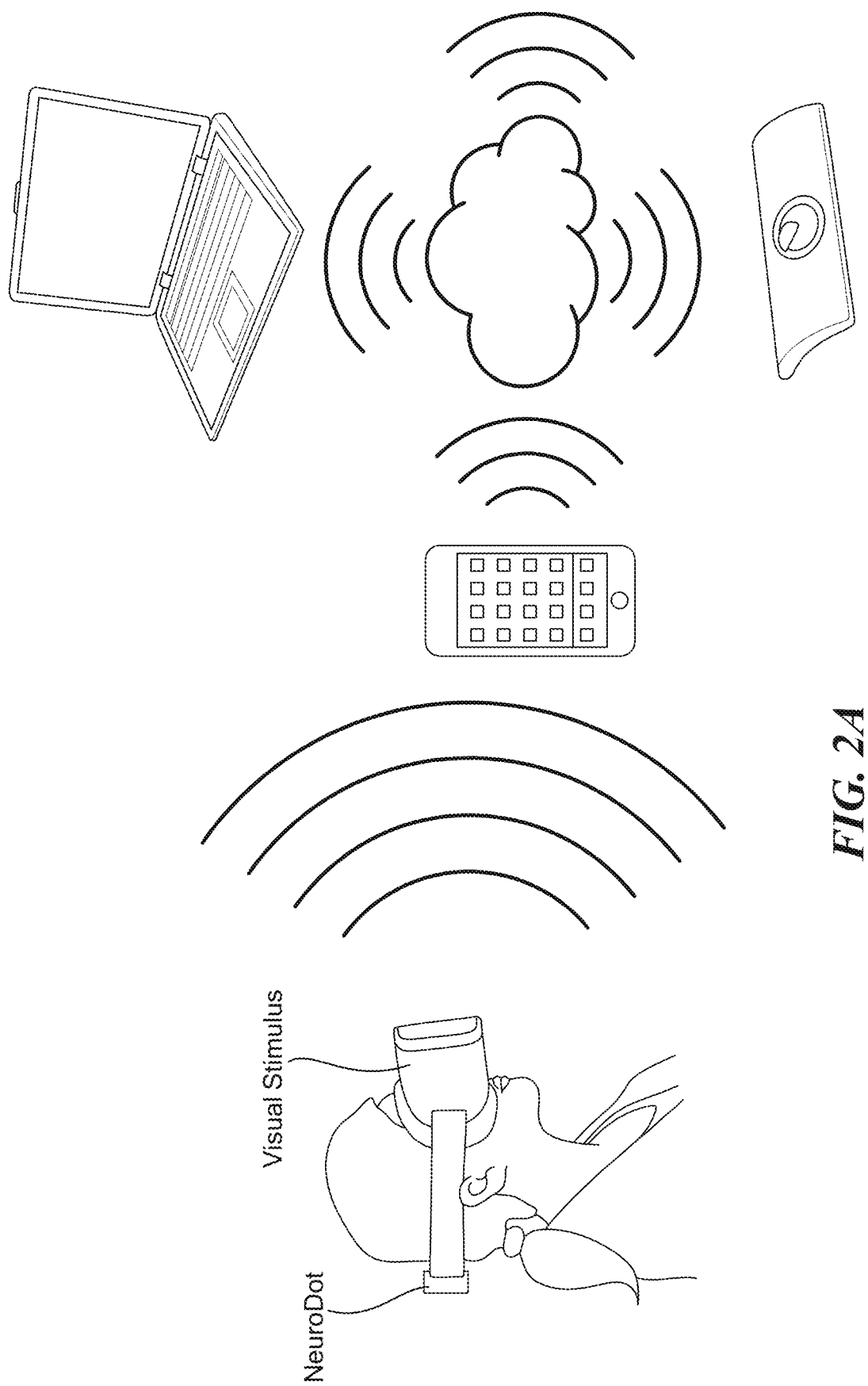
FIGS. 2A-2C show embodiments of a brain sensing theranostic system. The system embodiment shown in FIG. 2A uses a self-contained brain sensing theranostic headset device, including a head-mounted virtual reality headset, while the system embodiment shown in FIG. 2B includes a separate display unit in the form of a laptop computer display.
Figure 2B:
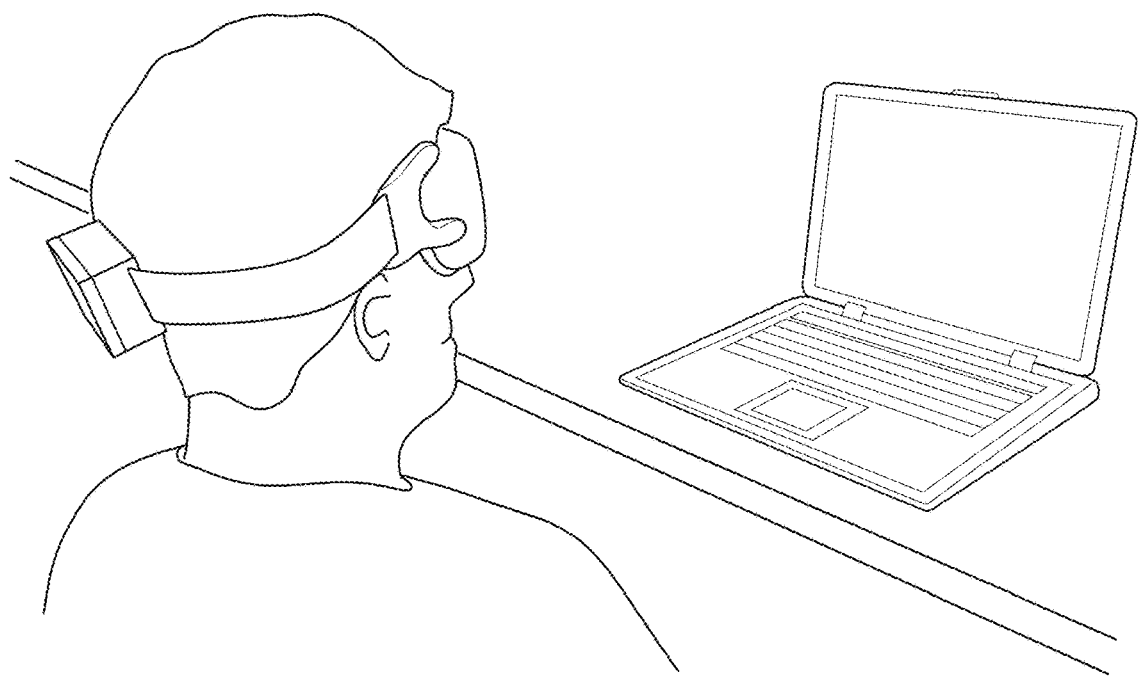
Figure 2C:
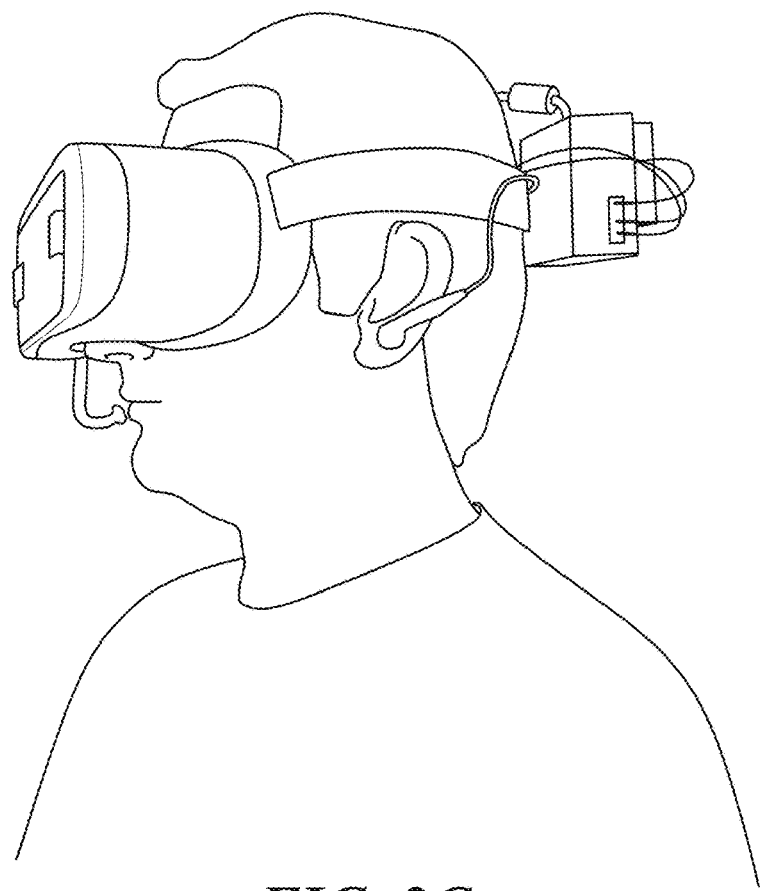

The presently described technology provides a new portable wireless electrophysiological sensor device and system to measure scalp potentials and fields using electric field encephalography (EFEG). The device functions as a high performance portable brain monitor and takes advantage of the EFEG modality and its relative advantages compared to EEG, including improved noise floor and signal-to-noise ratio (SNR), better localized sensitivity, and additional information content (field magnitude and direction). The device is capable of high quality recording of both transient and steady state visual evoked potentials and fields that have applications in analysis, diagnosis, and therapy of neurological and vision conditions.

The device of the present technology combines neurological readout via EEG, EFEG, or both, and visual display (including virtual reality or augmented reality displays) in a portable, wireless device that can be conveniently employed in medical applications, particularly for testing vision and brain function. Results have shown that the device is superior to commercial EEG devices in several ways.

Advantages of the present device include the following. The sensor circuit layout includes controller, amplifier, and electrode modules with small dimensions and improved noise reduction over commercial devices. The device uses an array of electrodes with low impedance, high stability and durability, and ease of use. The electrode design utilizes a functionalized coating of the sensing surface with silver/silver chloride nanoscale dendritic structure that leads to increased effective surface area and reduced potential drift. The coating is protected with a polymer hydrogel encapsulant, which reduces artifacts, improves referential stability, maintains a low impedance without the need for gels, and provides skin contact. The sensor unit offers a head mount design that is adjustable to ensure good contact with the head and includes a robust electrode mounting frame. The synchronization between the visual display unit and the sensor unit ensure low latency times and improve collection of data. The software architecture includes low-level device firmware, a radio-to-USB communication layer, a flexible high level Application Program Interface (API), an easy to use Graphical User Interface (GUI), and a collection of data post-processing and visualization scripts. The wireless implementation makes possible a variety of system configurations, wherein the device is either self-contained but reports data to a remote device, controlled by a local base unit separate from the headset, or controlled by a distant remote device through a network. Experimental results have shown that the device has improved signal-to-noise ratio (SNR), Berger effect detection, and classification accuracy when compared to commercial EEG devices.

The brain sensing theranostic headset device includes: a sensor unit containing an array of electrodes configured for providing electrical contact between the electrodes and the scalp of a subject wearing the device; a headband upon which the sensor unit is mounted, the headband being wearable on the subject's head and adapted for positioning the sensor unit adjacent to a selected brain region; and a display unit capable of displaying visual stimuli to one or both eyes of the subject. The device is capable of measuring signals from the brain of the subject in response to the visual stimuli. The signals include transient and/or steady state visual evoked potentials and fields (VEPF).

An embodiment of the sensor unit contains a modular circuit board stack which allows for more rapid design iteration; however, the components of the sensor unit can also be implemented on a single board. The three board stack-up includes a top controller module, middle amplifier module, and an electrode module at the base, which are coupled together using pairs of small form factor board-to-board mezzanine connectors. Four layer printed circuit boards and surface mount components were used where possible in order to keep dimensions small and improve noise reduction. The controller module has a socket for the microcontroller development board—Teensy 3.1 (ARM Cortex M4), 9V 600 mAh lithium rechargeable battery connection, low-noise linear 5V analog power supply, and optionally an nrf24l01+ wireless communication module (connection to the display or control unit via cable and USB port is also possible). The amplifier module accommodates the TI ADS1299 Analog Front End chip and its peripheral circuitry which amplifies and digitizes the signals coming from the electrode sensor array—this mixed signal board must be routed carefully with adequate shielding in order to minimize pickup artifacts at the sensitive high impedance analog input pins. The electrode module board was designed at half the width of the other modules in order to accommodate the head mounting bracket design and features mounting holes for up to 9 electrodes in a centered square electrode array footprint, which spans a 2×2 cm area. Also, the electrode module breaks out two external connections, the biopotential reference and the bias (driven ground), which use customized ear-clip electrodes on the left and right earlobes, respectively.

Figure 4:
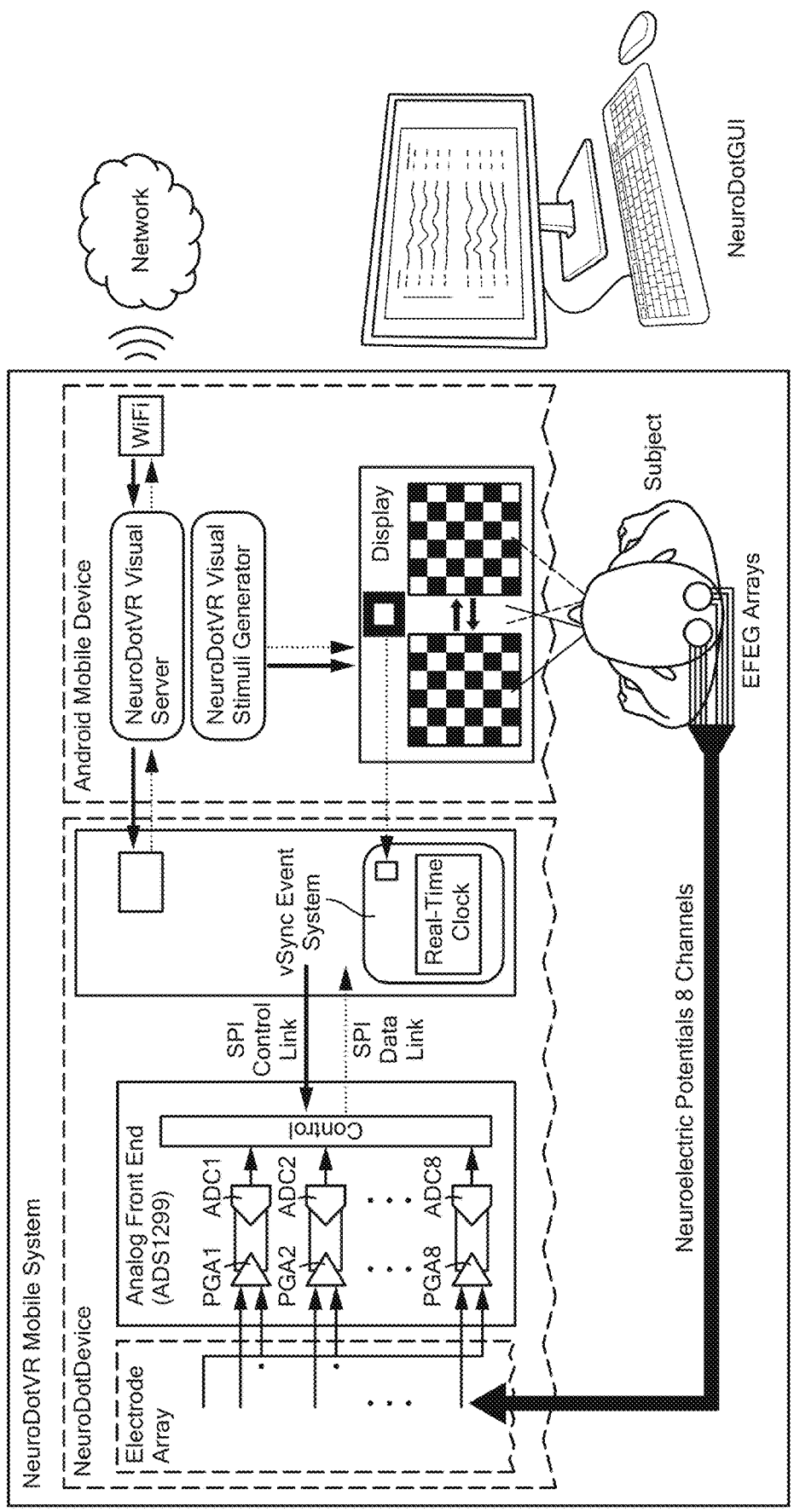
FIG. 4 is an electronic block diagram of an embodiment of a brain sensing theranostic system having a remote display unit. The diagram shows the component modules of the system and the flow of data and control signals.

The sensor unit can be configured to enable precisely timed event inputs in order to annotate the data stream for further post-processing. Event related potential (ERP) studies, based on averaging many time domain EEG/EFEG recordings of repeated stimulus presentations, rely on precise synchronization of stimulus and response within sub-millisecond resolution. The data stream is primarily composed of packets containing the biopotential samples from the EFEG array (4-8 channels) generated by the ADC circuitry (ADS1299) at a maximum rate of 1000 measurements per second. These records can be time-stamped at the moment they are received by the microcontroller on the remote device and are put into a data queue which gets sent asynchronously to a base station control and display unit, which then forwards these packets to the recording software on a personal computer over the USB port (see FIG. 4 for data/control flow diagram. During the initial startup period a back-and-forth radio communication is performed in order to synchronize the real-time clocks on the base station and remote device microcontrollers so that events received by both devices can be correlated. These clocks can be fitted with high precision quartz crystal oscillators which can be calibrated using Network Time Protocol (NTP) and adjusted using a firmware compensation mechanism in order to have a relative drift of less than ±1 millisecond per hour.

An event triggering system on the base station that inputs a low-latency digital signal interrupt to its microcontroller, which is used to generate a timing event data packet that gets inserted into the USB data stream. This digital trigger could be generated from a button switch where appropriate, e.g., for use in psychophysics paradigms. For VEPFs the signal is triggered by an optical sensor ("vSync" device) placed in the corner of the display so that a single video frame of the stimulus can encode a bit as two states of brightness (black/white) for a pixel patch covered by the sensor. By using 4 optical sensors to each measure a separate screen patch (which is either white or black), the vSync device allows for 14 user defined stimulus conditions to be signified, after reserving two special symbols "control" and "end". The "control" symbol allows for protocol extensions to multiple symbol commands (such as commands to automatically start and stop the recording program) and the "end" symbol marks the end of a given event's time span, known as the "epoch". The advantage of this direct-to-hardware trigger approach is the flexibility of input and display system choice without the need for complex peripheral and software driver installation on computer workstations.

In order to simplify the configuration of the device, the assurance of signal quality, the recording of data sessions, and the processing and visualization of data records, a software system architecture was created and was composed of low-level device firmware, a USB device to network communication gateway service, a flexible high-level Application Programming Interface (API), an easy to use graphical user interface (GUI), and a collection of data post-processing and visualization scripts. The device firmware, which runs on the Teensy 3.1 microcontroller boards, was programmed using the Arduino environment (based on the C++ programming language). The microcontroller streams data to and receives configuration commands from a network connection through the NeuroDot Gateway Service which runs on the USB-connected Android mobile device. The API layer, which is programmed in Python, runs on a Linux PC (although easily adapted to other platforms) and manages the communication with the NeuroDot Gateway Service. The Teensy 3.2 board on the Neuro Dot device provides a standard interface driver (CDC/ACM) that emulates a serial terminal over USB, through which commands can be sent and incoming data can be streamed at high speed. Commands sent from the API are usually relayed to the remote NeuroCotVR gateway device wirelessly through the local WiFi network, whereas responses to query commands and streaming data packets from the remote NeuroDot device travel in the other direction through the Gateway Service and then across the WiFi link to the API layer and perhaps upward to the GUI for display and recording. The API can be accessed through an interactive command line interface "neurodot_shell" which is mainly used to facilitate development and testing of device features. The "neurodot_gui" GUI application accesses device configuration functions and the packet data stream only through high-level API functions, a separation of concerns that greatly simplifies the user interface development.

The "neurodot_gui" application was developed using the Python language cross-platform Kivy framework, to simplify the use of our device ecosystem during benchmarking data collection trials. The efficient use of graphics hardware (through OpenGL libraries) enabled the application to smoothly stream up-to 8 channels of data at 1000 SPS with only a short lag, which is very useful for determining data quality as a result of adjustments made to the head-mounted device. A built-in impedance measurement utility also helps to quickly assure data quality before time is spent on long recording periods. During acquisition mode, the API layer is called by the application code to launch a parallel process to service the binary data streaming over the network connection (to the NeuroDot Gateway Service), which it decodes it into high level data types and places them onto a cross-process queue. The application features impedance measurements on all channels, integration of events triggered by the vSync device, efficient memory usage and disk-caching of the data streams to HDF5, an extensible standardized binary file format.

An embodiment of a wireless communication scheme uses a pair of nrf24l01+ 2.4 GHz (abbreviated rf24) digital radio modules between the remote and base station devices. A firmware protocol was developed in order to achieve the required 1000 SPS data rate with little to no dropout (given a clear line-of-sight) for the 8 channel 24-bit ADC samples and some header data. To facilitate efficient usage of the radio communications link, a custom firmware data link layer was developed that builds on top of the functionality provided by the open-source RF24 library which utilizes the Enhanced ShockBurst (ESB) protocol features of the nrf2401+ radio hardware. The ESB protocol handles the details of the packet construction, transmission, and reception over the 2.4 GHz band carrier channel and provides mechanisms of error detection, acknowledgement, and resending of lost packets; radio state changes are signaled by a dedicated interrupt line and data is transferred to and from the MCU over an SPI bus. The maximum effective data throughput is estimated to be 64 kBytes, more than sufficient for the required maximum data streaming rate of 32 byte packets (for each 24-bit 8 channel sample plus timestamp and status bytes) at 1000 SPS. Two sensor units together can be in one of two radio communication modes, dialog or streaming. Radio messages are received and sent on control from hardware interrupt signals to minimize latency and packet loss and are buffered by incoming and outgoing circular queues, respectively. In each device's main loop, the code periodically checks the queues and the radio state and transmits outgoing messages or calls the appropriate handler function for incoming messages. In dialog mode, which is used for configuration, each device's radio is by default in a listening state and transitions to transmitting state only when a message data packet is waiting on the outgoing queue; e.g. the base station transmits after a command from the API coming over the USB interface queues an outgoing message. In streaming mode, the remote device continually receives signal samples from the ADS1299 hardware on interrupt when a conversion is complete and puts the data packet on the outgoing queue; while in this mode the Remote device's radio never enters the listening state but it can be signaled to transition back to dialog mode upon receiving a stop message contained in the Base Station's acknowledgement (ACK) packet. Table 3 below provides a summary of the specifications and features of the NEURODOT prototype EFEG sensor system.

The present brain and vision monitoring device is well suited for use in a variety of field, clinical, and commercial test situations due to the portable configuration and compact size of the device, its utilization of wireless technology, quick set-up capability, robust and low noise electrode performance, and its ability to record in both EEG and EFEG modes. The device is suitable for diagnosing and treating a wide variety of medical conditions, particularly conditions involving visual impairments and neurological conditions involving the brain. It can be quickly set up and used, for example, in any position, upright or reclined, and can be deployed in any environment as battlefields, trauma centers, field hospitals, homes, or ambulances. An 8-electrode sensor unit array can cover the entire visual cortex. The display unit can provide monocular, dichoptic, stereoscopic, binocular, hemifield, multi-focal, static, dynamic and chromatic stimuli, as well as stimuli involving virtual reality or augmented reality scenes or video environments. The device can perform simple vision tests, tests of mental activity or reaction, as well as tests or therapeutic protocols using adaptive algorithms that update the stimulus in real time. In diagnostic tests, the device offers objective results unbiased by the subject's perception or communication ability, including language skills. A variety of specific visual stimulus protocols have been developed, which can be used in diagnostic and/or therapeutic applications, as described further below.

The brain and vision theranostic device and system can be used by optometrists and ophthalmologists to diagnose and treat a wide variety of vision defects. These include glaucoma, macular degeneration, amblyopia, malingering, optic neuritis, strabismus, convergence insufficiency, and color vision anomaly. The device and system also can be used in clinical evaluation of conditions of the brain, particularly conditions related to traumatic injury, neurodegenerative disease, or ischemic conditions. Brain conditions that can be diagnosed include traumatic brain injury, concussion, encephalopathy, multiple sclerosis, dyslexia, dementia, attention deficit hyperactivity disorder (ADHD), Alzheimer's disease, Parkinson's disease, Huntington's disease, amyotrophic lateral sclerosis, cerebral ischemia, and stroke. The device and system also can be used to test the effects of new drugs on the brain or on vision, such as during clinical trials of drug candidates for FDA approval. Additional uses are in gaming, particular associated with virtual reality or augmented reality environments, and neuromarketing, where consumer reactions to products are evaluated objectively.

Table 1 lists a variety of stimulus types which are in use with previously available EEG technology and the clinical situations in which they are employed.

TABLE 1

Description of visual stimulus types

| Stimulus type | Clinical Application |
| --- | --- |
| Steady State VEP (ssVEP) rapidly repeated pattern at a single frequency | Visual field and acuity, and various applications in BCI |
| Sweep VEP Alternated pattern stimulus, 5 to 15 Hz, producing ssVEP. Within 10 seconds, 20 different pattern sizes or contrasts are presented in succession. The smallest pattern size or lowest contrast producing a response allows an estimation of visual acuity or contrast sensitivity. | Acuity testing, contrast sensitivity assessment, nonverbal patients (children or adult) and malingering patients |
| Motion VEPs Motion processing involves the magnocellular and dorsal pathways. Four types are used: Motion-onset VEPs, Motion-Reversal VEPs, Motion-Offset VEPs, Chromatic Moving Stimuli. | Diagnosing CNS disorders including multiple sclerosis, encephalopathies, dyslexia, optic neuritis and glaucoma |
| Chromatic (Color) VEP The alteration in color pattern reversal visual evoked potential (CPR-VEP) by using various temporal frequencies with different color stimulations (black/white, red/green, and blue/yellow) | Color vision anomalies, glaucoma visual function damage |
| Binocular (Dichoptic) VEP Each eye is presented with separate visual stimuli by alternating field stereoscopy of the system. Binocular stimuli of three kinds are presented: (1) Dynamic random dot correlograms (2) Dynamic random dot stereograms (3) Dichoptic checkerboard stimuli. | Objective evidence of cortical binocularity, Preoperative gradation of binocular potential, and prediction of postoperative binocular fusion [Error! Bookmark not defined.], oculmotor alignment, strabismus and convergence insufficiency. |
| Multichannel VEP For multichannel VEP, the recommended pattern stimulus is presentation of field of 30°. A minimum of two channels and at least three active electrodes, two of the lateral ones located at O1 and O2, and a third midline active one at Oz is required for detection of lateral asymmetries. The reference for all the active electrodes should be Fz. Ancillary electrodes at PO7 and PO8 also referred to Fz may augment the sensitivity to lateral asymmetries. | Avoid paradoxical lateralization, study lateral asymmetries |
| Hemifield VEP The P100 waveform recorded from inion is algebraic sum of individual half-field VEPs. On hemifield stimulation, the ipsilateral visual cortex reveals the positivity whereas on the contralateral side and a negativity is recorded. The majority of P100 is generated by the lower half of the central field and the upper visual field may contribute as negative peak at frontal location. | Hemifield stimulation may reveal lesion in visual pathway in spite of normal full-field PVEPs, with higher sensitivity than full-field testing in identifying lesions at chiasmal or postchiasmal sites. |
| Dark Adaptation VEP Following a photobleach, ssVEPs are measured as a function of checkerboard luminance every 20 seconds. The lowest luminance producing a response at each time point measures dark adaptation recovery. | Photosensitivity and retinal pigment epithelium damage. |

TABLE 1-continued

Description of visual stimulus types

| Stimulus type | Clinical Application |
|---|---|
| Multifocal VEP (mfVEP) Steady state VEPs are recorded simultaneously from many areas of the monocular and binocular visual field with the multifocal technique. The patient looks at a display having multiple sectors. Each of the sectors of the display is an independent spatial and temporal stimulus. Frequency tagging methods combined with control of acuity, contrast, color, depth or motion in each sector allow the rapid generation of a map of specific defects. This map is in the form of a probability plot similar to the one used to display visual field defects measured with automated perimetry. | Evaluation of monocular or binocular visual field defects that may arise from any retinal, optic nerve or cortical dysfunction in central or peripheral vision. Can be used in the diagnosis and follow-up of patients with a broad range of optometric and ophthalmic disease and monitoring progression of the disease. |
| Eye Tracker Video-based eye tracking built in to the Neurodot HMD, used to ensure accurate retinotopc placement of visual field stimuli, and to measure vergence (binocular testing), fixation stability, smooth pursuit (motion testing), optokinetic nystagmus, saccadic latency & amplitude, and anti-saccade suppression. | Oculomotor control & compliance, strabismus and convergence insufficiency, cognitive impairment, malingering. |

Table 2 below presents protocols for diagnosis of specific vision conditions which can be implemented with a brain sensing theranostic headset device or system of the present technology. The table indicates which type of VEPF protocol is suitable.

TABLE 2

Portable diagnostics of opthalmic indications

| Indication | Method | Visual Stimulus | Test Duration |
|---|---|---|---|
| Visual Acuity | Swept acuity ssVEPF | Sine wave gratings, 100% contrast, increasing spatial frequency | 10 seconds per eye |
| Visual Defects/Loss | Multifocal VEPF | Log polar Checker-board, 16 sectors per eye | 3 minutes per eye |
| Contrast Sensitivity Function | Swept contrast ssVEPF | Sine wave gratings, decreasing contrast, 5 spatial frequencies (1,2,4,8,16 c/deg) | 50 seconds per eye |
| Traumatic Brain Injury | Swept acuity ssVEPF Swept contrast ssVEPF, Multifocal VEPF, DA VEPF, Binocular VEP | Sine grating varying in spatial frequency or contrast, checkerboard varying in luminance or contrast | Acuity-10 sec, Contrast 50 sec, mfVEP 50 sec, DA VEP 15 minutes, binocular VEP 30 sec |
| Concussion | Swept Acuity VEPF, Swept-Contrast VEPF, Dark Adaptation VEP, Binocular VEP | Sine wave gratings, checkerboard sectors varying in luminance | Acuity, 10 sec, Contrast 50 sec, DA, 15 minutes |
| Malingering | Swept-Contrast VEPF, Eyetracker | Sine wave gratings | 50 seconds per eye |
| Amblyopia | Swept-Contrast VEPF | Sine wave gratings | 50 sec per eye |
| Glaucoma | Multi focal VEPF | Checker-board sectors varying in contrast | 3 minutes |
| AMD | Dark Adaptation Recovery | Checker-board sectors varying in luminance | 15 minutes |

TABLE 2-continued

Portable diagnostics of opthalmic indications

| Indication | Method | Visual Stimulus | Test Duration |
|---|---|---|---|
| Multiple Sclerosis | Swept Acuity VEPF, Swept-Contrast VEPF, Multi focal VEPF | Sine wave gratings, Checker-board sectors varying in contrast | Acuity, 10 sec, Contrast 50 sec, mfVEP 3 minutes |
| Optic Neuritis | Swept Acuity VEPF, Swept-Contrast VEPF, Multi focal VEPF | Sine wave gratings, Checker-board sectors varying in contrast | Acuity, 10 sec, Contrast 50 sec, mfVEP 3 minutes |

Amblyopia can be detected by a significant difference between the dominant and the non-dominant eye of the first harmonic power in the potential evoked by gratings reversed at 5 and 10 Hz [19]. Short- and middle-latency evoked potentials have been shown to effectively predict coma outcomes in patients with acute traumatic brain injury (TBI). Long-latency event-related potential components can be used in predicting recovery of higher order cognitive abilities in TBI [20]. Contrast sensitivity deficits are also diagnostic for TBI as well as concussion. In cases of asymmetric glaucoma, short duration transient VEP (SD-tVEP) results correlate significantly with the level of visual field damage as measured by macular degeneration [21]. In the eyes with more advanced visual field loss, reduced SD-tVEP amplitude is associated with decreased macular thickness on ocular coherence tomography. Thus, SD-tVEP can be used as a fast and objective method to assess or screen for functional damage in glaucomatous eyes.

EXAMPLES

Example 1. Prototype Brain Sensing Theranostic Headset Device

A prototype NeuroDotVR sensor system was prepared including two arrays of 4 small-diameter (<6 mm) biopotential electrode pins arranged in a centered-square grid. Each pin connected to its own amplifier channel (see FIG. 4), which amplified the potential difference between it and a separate reference electrode. In the EFEG mode, a central sensor (9th) pin could be used as a shared local potential reference for all the amplifier channels, but in order to simultaneously record in EEG mode, the system was configured with a global ear-clip reference (typically on the left ear-lobe). The sensor system also used another special electrode called the "bias electrode" (typically clipped on the right ear-lobe) which served as an active ground, adjusting the global potentials to mid-amplifier supply range, and additionally providing common-mode noise-cancellation through a feedback loop provided by a Texas Instruments ADS199 chip.

The average potential of the symmetric array (with respect to the remote reference) Vavg, is analogous to a single EEG channel at the center of the array, albeit with lower noise. In this montage, local electric field components can be estimated via local gradients about this central potential—the polarity of which is independent of the remote reference location. With the assumption of approximate linear variation over the small length scales of the array, the determination of the electric field components tangential to the scalp are treated as the parameters in a 2-dimensional linear fitting problem. Further, with the spatial symmetry of the array, the calculation of the electric field components from the n (=4) gradient measures their weighted sum simplifies to:

$$EFEG: E_{x,y} = \frac{\sum_{i=1}^{n} \Delta F_i \cdot x_i}{\sum_{i=1}^{n} x_i^2} \quad (1)$$

$$EEG: V_{avg} = \frac{\sum_{i=1}^{n} F_i}{n} \quad (2)$$

where index i runs over the n sensor pins, $x_i$ stands for the x-coordinate of the pin with respect to the center of the array, and $\Delta F_i$ stands for the sampled potential difference between the i-th pin sensor and the central reference value Vavg at any given time step. The same sensor can also be used simultaneously in a more traditional EEG mode using formula 2 above with a specified reference electrode (such as a left ear clip).

The EFEG regime is most useful when estimating local brain activity which varies spatially in the vicinity of the sensor, and unlike EEG, EFEG is free from the ambiguity of choosing the potential reference [15]. Spatially homogenous neuroelectric potentials are deemphasized by the field-based signal processing. Furthermore, EFEG eliminates any signal or noise components that couple evenly to all measurement channels, so called "common-mode" components, including off-target bioelectric signals, external electromagnetic interference, or reference channel artifacts, which could account for improved robustness against these correlated sources of noise. However, variations in coupling, such as mismatched channel impedances can reduce this common-mode rejection, so these artifacts may still show up with reduced magnitude. The key to leveraging this new modality effectively will be to ascertain which experimental paradigms take advantage of the complementary signal to noise relationship.

Some characteristics of the prototype device are summarized in Table 3.

TABLE 3

| NeuroDot Sensor specifications | |
| --- | --- |
| Number of channels | 4 or 8 channels per sensor |
| Electrode fixture area | 2 × 2 cm area |
| Weight per sensor | 90 g |
| Local Processor | ARM Cortex M4, 96 MHz |
| Recording Rate | 1000 SPS |
| Electrode Spacing | At 0.7 and 1.0 cm spacing on centered square grid |
| Electrode Design | Custom robust hydrogel-encapsulated Ag/AgCl pogo pins; Typical impedances <100 kOhms |
| EFEG | 4 or 8 channels reduced to $E_x$ & $E_y$ |
| EEG | Requires ear clip reference |
| Usable Neuroelectric Bandwidth | 0.5 Hz to 500 Hz |
| Internal Noise | <0.5 $\mu V_{p-p}$ for gel-shorted measurement. |
| ADC Resolution | 24 Bits |
| Input impedance | $10^{10}$ Ω |
| Data Throughput | 32 kB/s (including sub-millisecond accurate timestamps) |
| Battery Life | ~4 Hours with 600 mAH lithium rechargeable battery, easily swapped out |
| Overall SNR improvement | EFEG outperforms EEG by up to 4X in some metrics of SNR |
| Portable | Yes |
| Wireless | custom protocol using nrf24101 + radio (2.4 GHz band) |
| External Trigger Synchronization | real-time clocks with compensated drift <1 ms/hr. |

Example 2. Measurement of Pattern Reversal tVEPF

Participants viewed 16 sets of 16 trials for a total of 256 identical stimuli patterns composed of a black and white checkerboard having 64 rows and 64 columns and check size of 0.25° (when viewed from a distance of 70 cm), which appears on top of a neutral gray background and reverses check-color 500 ms after the onset. A pause of approximately 10 seconds was given between sets and participants were instructed to keep their eyes open and minimize movements during the recording of each stimulus presentation.

Figure 5:
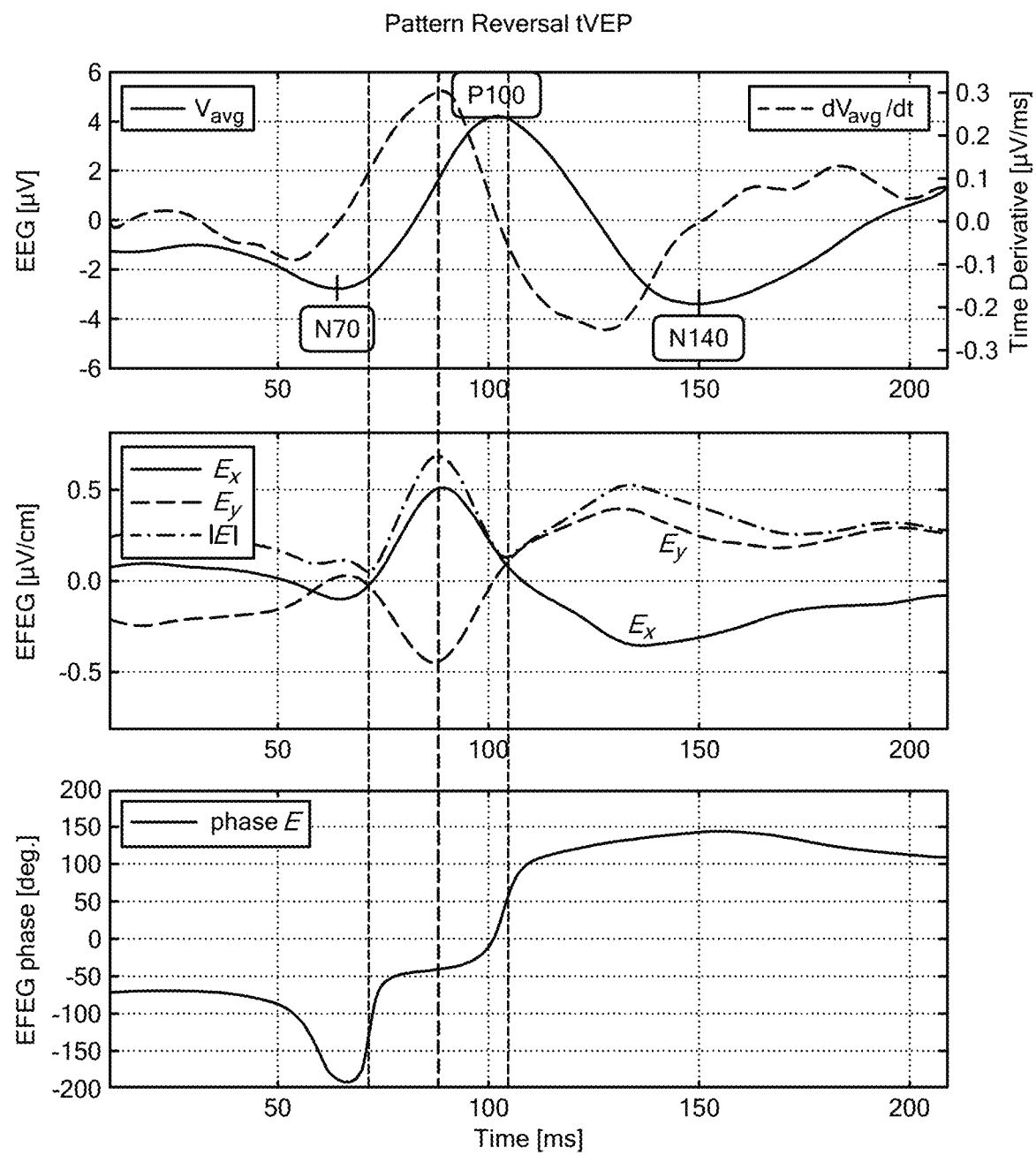
FIG. 5 shows sensor results for pattern reversal tVEPF. Top panel: EEG signal [$\mu V$, left axis] showing the well-known N70, P100 and N140 features and its first order time derivative [$\mu V/ms$, right axis]. Middle panel: Ex, Ey components and magnitude [$\mu V/cm$] of the EFEG electric field show local extrema correspondence to EEG time derivative peaks and inflection points. Bottom panel: EFEG phase [degrees] showing rapid shifts between steady states corresponding to above features.
Figure 6A:
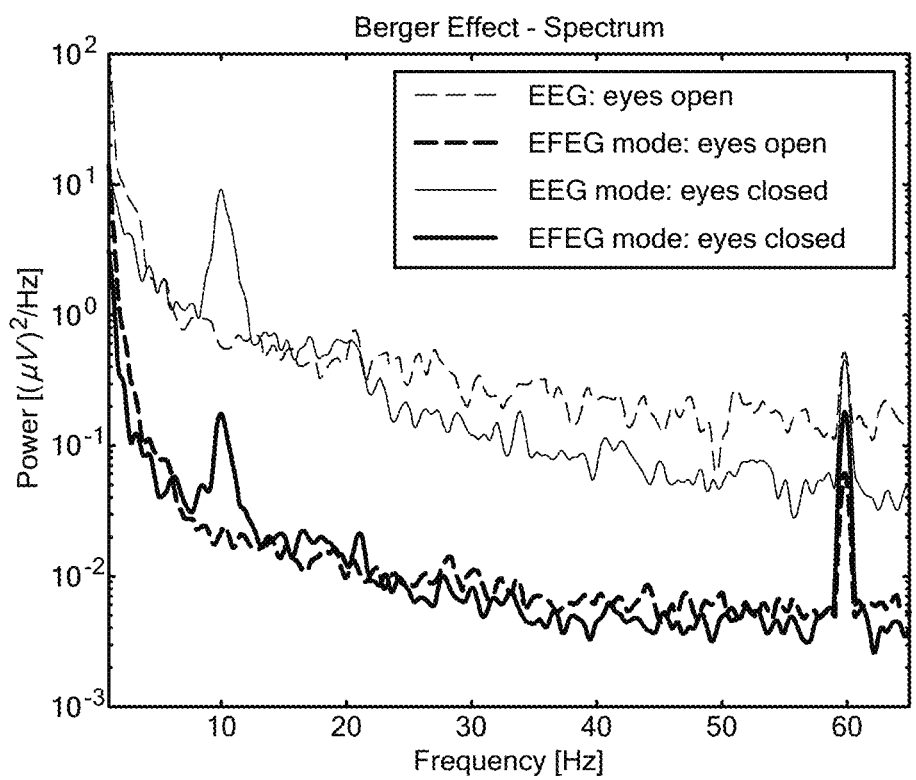
FIGS. 6A and 6B compare ssVEPF results obtained in EEG vs. EFEG modes.
Figure 6B:
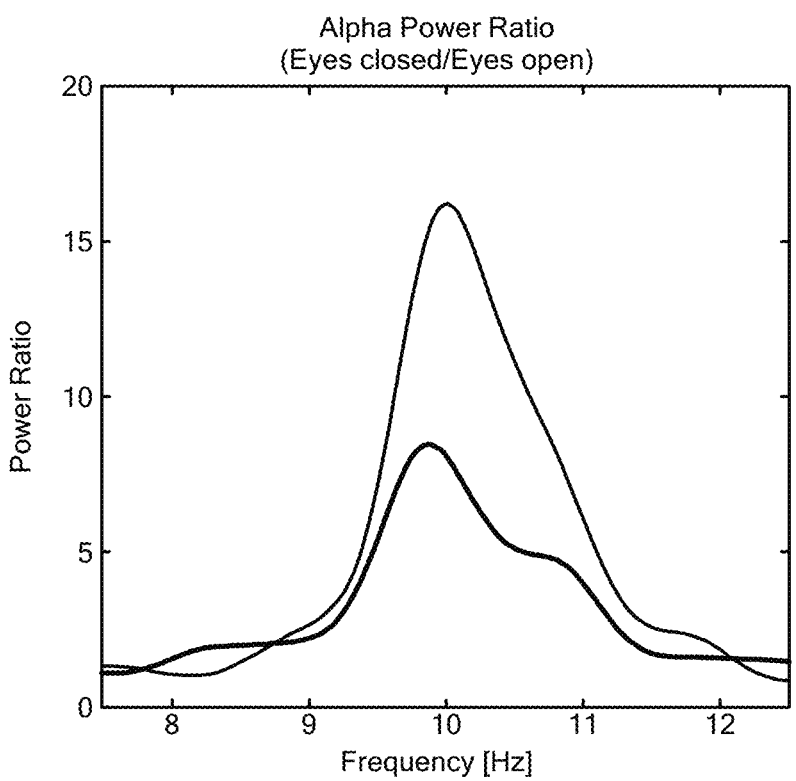

Using the same lower, left occipital lobe position (O9) and 4-channel array as in the ssVEPF experiment (below), potential signals referenced to the left ear-clip electrode were collected at 1000 SPS, yielding a 1 ms time resolution. The recorded signals were 4th order Bessel bandpass filtered between 1 and 55 Hz and 4th order Butterworth notch filtered between 59-61 Hz. Timing events from the vSync device were used to divide the signal into epochs lasting approximately 200 ms after the pattern reversal; the potentials were averaged over the 4 channels, filtered to exclude epochs with maximum amplitudes greater than ±10 μV, and were averaged together in the time domain to form the tVEP. Additionally, EFEG mode signals were computed from the filtered potentials and averaged over the same epochs. The main three prominent peak polarizations associated with the pattern reversal tVEP are evident in the EEG mode potential data (FIG. 5, top left axis) labeled: N70 (negative, ~70 ms), P100 (positive, ~100 ms) and N140 (negative, ~140 ms, though occurring around 150 ms in this case). The EFEG data (FIG. 5, middle and bottom) shows an interesting feature where the components undergo an abrupt change in phase and magnitude which peaks around 88 ms. The maximum peak in EFEG magnitude occurs before the EEG P100 and is associated with rapid changes of in the relative phase of the Ex and Ey components of the electric field; this feature seems to correspond directly to a peak in the first time derivative of the potential (top right axis at dashed line) and the preceding and following minima seem to correspond to inflection points as well as the abrupt phase changes (dotted lines). Since EFEG is analogous to a spatial derivative (gradient of the potential), this correlation with the time derivatives of potential lends evidence to a hypothetical wave or diffusion of cortical activation. Thus the sensor not only provides high quality pattern-reversal data in the EEG mode similar to that used clinically for VEP studies, but also provides entirely new information, electric field magnitude and direction, in the EFEG mode. Furthermore, the EFEG signals emphasize local cortical processes and are free from the ambiguity in choice of reference location, which affects the polarity and relative magnitudes—and thus the interpretation—of EEG time domain signals.

Example 3. Multiple Location tVEPF

Two four-electrode EFEG arrays were placed over the optical cortex 10-20 system locations O1 and O2, the rightmost two of the O1 electrode group and leftmost two of the O2 electrode group were used to compute the central Oz location. 90 trials of dichoptic pattern reversal checkboard stimuli evoked neuroelectric data were averaged to produce standard VEP (thick line) as well as the EFEG based VEF signals Ex (blue) and Ey (red), the horizontal and vertically aligned electric field components. tVEPF data for the left eye trials are plotted separately from the right eye trials, which is a useful discriminant in visual function assessments. Unlike the tVEP pattern which has a doubled peak in the P100 region, the EFEG signals (tVEP) show an interesting pattern that is smoother and less ambiguous to interpret. The Ex peak polarizations around 80 ms are stronger than that of the Ey components for the two outer locations O1 and O2 (for both eyes), and they are opposite in directionality meaning that the electric field is simultaneously pointing inward (towards head center) at that moment. In the Oz (center) location the Ey polarization is stronger but is opposite in directionality between the two eyes. The tVEF patterns contain much more information than the standard tVEP.

Example 4. Simultaneous EEG/EFEG Spectral Comparison

The EFEG components $E_x$ and $E_y$ (which are usually represented in units of $\mu V/cm$) are computed from the slope components of a 2D linear surface (with intercept equal to $V_{avg}$) along with the geometry parameter, d=1.5 cm (pin spacing from center of 4-electrode array). In order to rescale EFEG to the same dimensions as EEG, multiply by the geometry parameter d. To better account for relative spatial phase information in the frequency domain the complex Fourier transform of the EFEG components can be taken in quadrature, $E=E_x+iE_y$, which produces a two-sided spectrum that is mapped back to only positive frequencies by averaging in the corresponding negative frequencies. On the other hand, computing the magnitude of the EFEG signal $|E|=\sqrt{E_x^2+E_y^2}$ is a nonlinear process which causes doubling of frequency components and loses phase information—so this signal is not typically computed when doing frequency domain analysis—although this signal might be of more use in time domain representations.

The Berger Effect is a simple paradigm that measures the attenuation of the intrinsic Alpha rhythm in the visual cortex due to light-adaptation. A single individual's response at the center of the occipital lobes (Oz in the 10-20 system) was measured for 30 s with eyes open looking at a fixed black and white checkerboard pattern of 64×64 squares on a neutral-gray background displayed on a typical LCD monitor (full brightness, pattern spanning ~30 cm of ~70 cm screen, subject at distance ~70 cm, within a typical office fluorescent lighting environment), followed by 30 s with eyes closed.

Figure 7A:
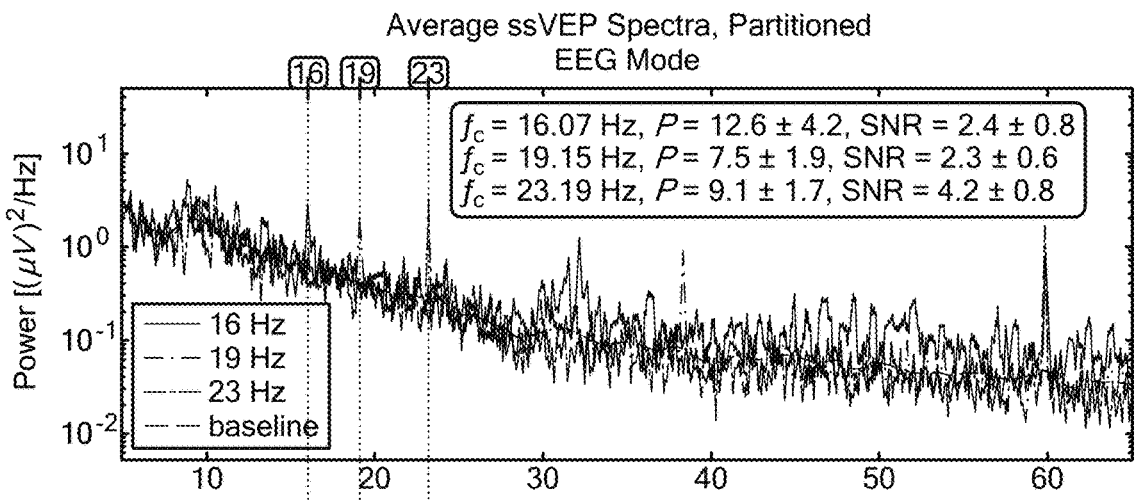
FIGS. 7A and 7B show ssVEPF spectra for EEG (7A) and EFEG (8B) modes obtained with the sensor for 16, 19 and 23 Hz reversing checkerboard stimulus frequencies. The EFEG signals have about 1/10 the magnitude of EEG signals, though their signal-to-noise ratios (SNR) are higher.
Figure 7B:
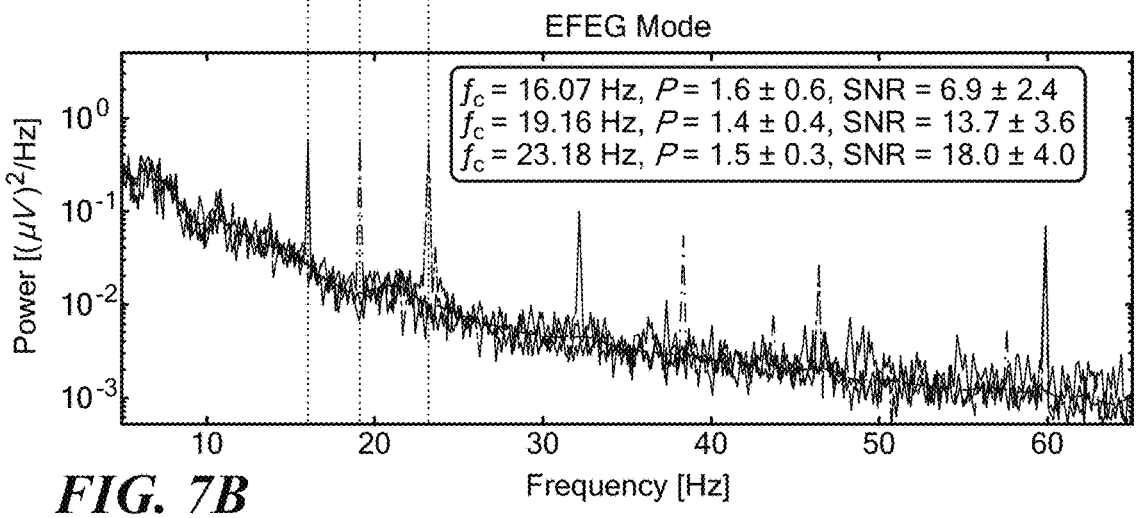
Figure 7C:
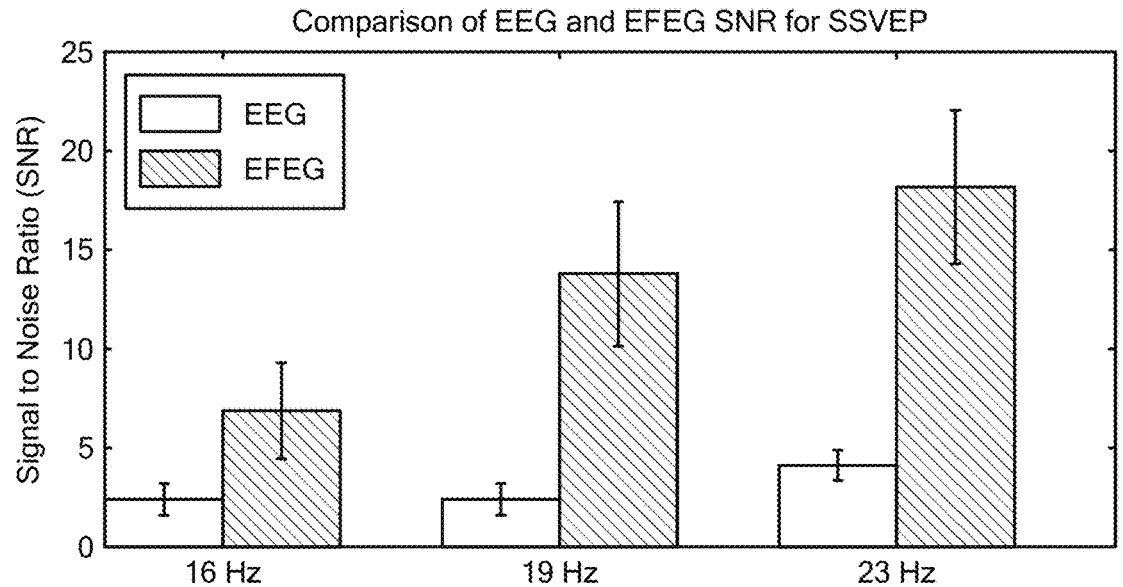
FIG. 7C presents a comparison of signal-noise ratio (SNR) showing 3- to 4-fold superior performance of EFEG over EEG modes for this paradigm.

The EEG and EFEG modalities are compared in FIGS. 7A-7B. Power spectral densities (PSD in units $\mu V^2/Hz$, FIG. 7A) were computed using Welch's Modified Periodogram method with a half-overlapping spectral window of length $2^{13}$ samples. To better account for EFEG's relative spatial phase information in the frequency domain we use the complex Fourier transform of the field components taken in quadrature, E=Ex+iEy, which produces a two-sided spectrum that was mapped back to only positive frequencies by averaging in the negative frequency components. The EFEG spectral baseline tends to be over an order of magnitude lower than the averaged EEG baseline—this can be attributed to the dominance of biological background sources during subject testing which must be largely homogenous over the span of the electrode array. The ratio of eyes closed to eyes open spectra in the Alpha band (FIG. 7C) illustrates that the SNR of EFEG is somewhat smaller than that of EEG in this case—which might imply that this subject's Alpha waves do not vary strongly over the space of the sensor electrode array (spanning 2 cm vertically and horizontally) located at position Oz. An elevated noise-floor is visible in the EEG eyes open data, which is known to be caused by small movement artifacts being included during that phase of spectral estimation; however, the simultaneously recorded EFEG data has a noise floor which is closer to that of its eyes closed counterpart, demonstrating that the EFEG signal is more robust against movement artifacts.

The sensor was benchmarked for a variety of ssVEPF stimuli. Participants viewed stimuli displayed on a monitor composed of a reversing black and white checkerboard having 64 rows and 64 columns with a check size of 0.25° (when viewed from a distance of ~70 cm), alternating at frequencies of 16, 19 or 23 Hz and lasting for a duration of 10 seconds per trial. Trials were arranged into 3 blocks with 3 sets of each stimulus condition, presented in random order for a total of 9 trials each. Between stimuli presentation blocks, participants were able to take a break until they were comfortable to proceed. Participants were instructed to keep their eyes open and minimize movements during the recording of each trial. A 4-channel electrode array was placed on the location O9 (10-20 system, lower left occipital lobe) which was found in pilot studies to maximize the SNRs. The signals were recorded at a rate of 500 SPS and were processed in two distinct modalities: the average potential over the channels is represented as "EEG mode" referenced to the left ear-clip electrode; the spatial gradient is represented as "EFEG mode" which is reference-less; for EFEG mode spectral estimation, the average of the negative and positive sides was taken for the complex quadrature signal E·d=Ex·d+i·Ey·d, where d=1 cm. Timing events from the vSync device were used to partition the recording into epochs associated with each frequency condition. Power spectral density (PSD in units μV2/Hz, FIGS. 7A, 7B) was computed in EEG and EFEG modes for each epoch using Welch's Modified Periodogram method with half-overlapping windows size of 213 samples and then averaged together with epochs of the same stimulus class, color coded: red=16 Hz, green=19 Hz, blue=23 Hz. A spectral "noise" baseline (dashed black curve, FIGS. 7A, 7B) for SNR calculation was computed by taking the median value across the three partitioned average spectra and then smoothing with a moving median filter and Hanning kernel convolution both of window length 25. For each stimulus frequency peak, the centroid frequency fc, total power P, and signal-to-noise ratio SNR was measured using data in a 0.5 Hz wide band about the center. It is clear that in this situation the EFEG mode yields a much higher SNR than EEG as well as showing definite second harmonic peaks and a cleaner baseline, which can be attributed to an increased sensitivity to neuroelectric spatial variations while rejecting noise that is common to all channels. Similar relative performance was achieved for 3 other subjects, but peak amplitudes were subject specific and somewhat variable among repeat experiments.

Example 5. Fabrication of Semi-Dry Electrodes

Figure 3A:
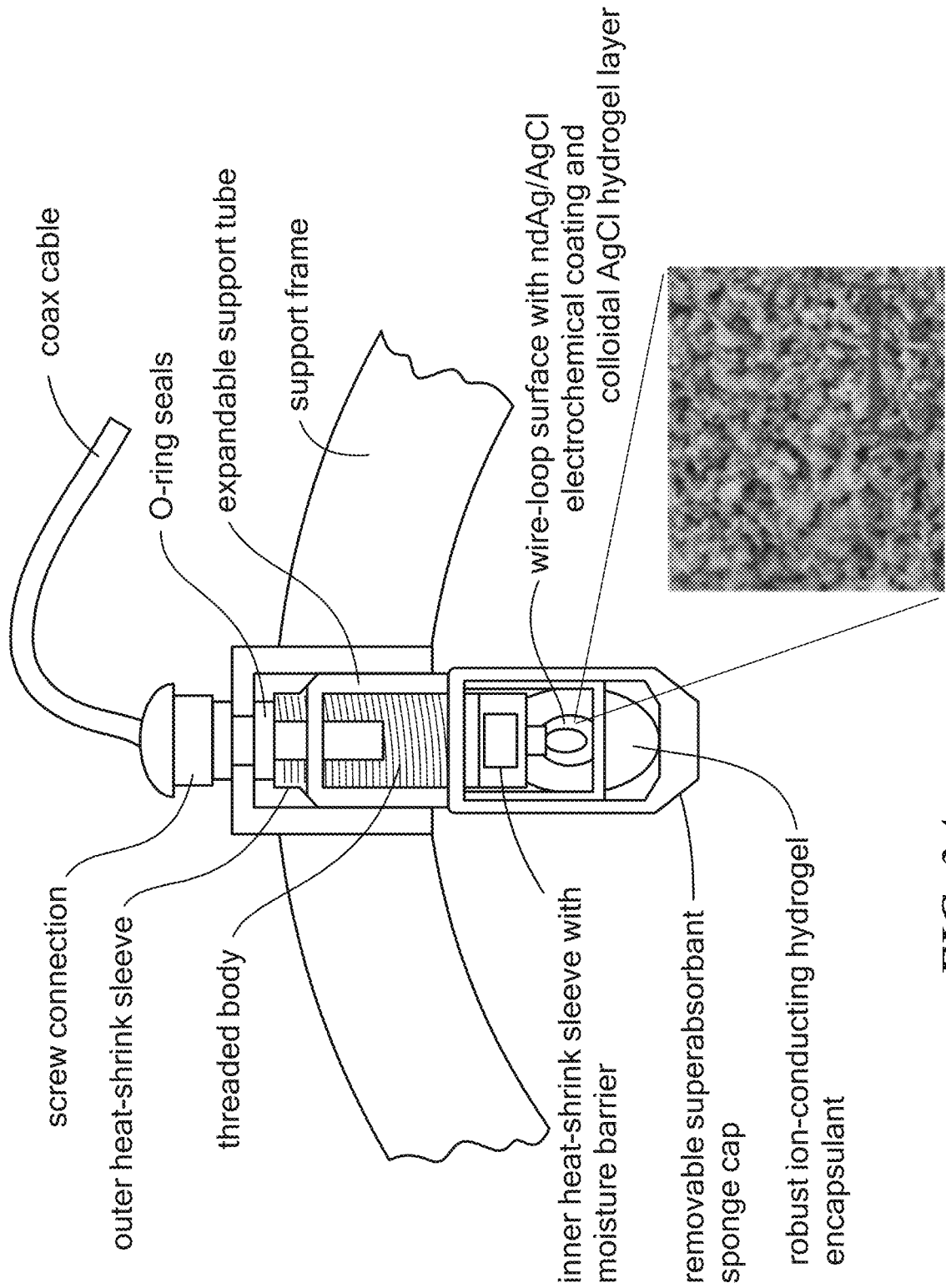
FIG. 3B shows a scanning electron micrograph (SEM) image showing the nanodendritic surface texture of the electrode Ag/AgCl coating.
FIG. 3C shows a CAD model of a support frame for an electrode array. Dark circles represent holes for electrode insertion and the lines show the electrode alignment. Scale is in millimeters.

Small footprint, robust yet soft-contacting electrodes for neuroelectric monitoring were fabricated. A schematic illustration of a cross-section of such an electrode is shown in FIG. 3A. The electrodes are suitable for repeatedly measuring small differences in signals between very closely spaced electrodes with low impedance contact with the scalp.

The electrodes utilize formulations of nanoparticle-enhanced ion-conducting polymer hydrogel encapsulant material, which functionalizes a metallic substrate (typically a silver wire) into an external biopotential electrode that is an efficient transducer of biologically generated ion currents into electronic currents suitable for low noise signal recording. In use, the electrodes are wetted with a saline solution and are capable of producing low skin-contact impedances (<200 or <100 kOhms) over a small area (typically <6 mm diameter). Pairs of these electrodes showed small initial potential offsets (<1 mV) with drifts of less than 1 μV/s. The exceptional potential stability relates to use of silver chloride (AgCl) nanoparticle dispersions (up to 10 wt %) in conjunction with polymer-stabilized graphene particles at low concentrations (~1 wt %) intercalated within a mechanically robust ion conducting hydrogel matrix. The inner coating layer containing AgCl and graphene particles, when applied to a silver substrate, forms an Ag/AgCl electrocouple with a highly stable reference potential that is enhanced by the graphene additive, which facilitates electron transfer. Further, the electrode is encapsulated with another layer of the hydrogel material, the outer-coating layer, which does not contain AgCl nanoparticles but may optionally contain graphene particles. Optionally, the outer coating layer can be formulated as an anion selective membrane for control of osmotic properties when used in conjunction with an external chloride bearing saline skin conductivity enhancement solution. A removable superabsorbent sponge cap is applied to the tip of the electrode and serves to hold the saline conductivity aid near the skin as well as forming a compliant and comfortable mechanical contact with the scalp.

The hydrogel formulation includes a high concentration of highly hydrolyzed polyvinyl alcohol polymer (PVA, 15-20 wt %, with medium-high molecular weight 89-98 kDalton and >98% hydrolyzed) that—when blended with the electrolyte solution and particle additives—creates a robust, elastic mechanical framework and porous hydrophilic matrix containing an ion-conductive electrolyte phase. One half of the polymer powder is dissolved into the aqueous electrolyte component after optional graphene compounding and the other is dissolved into deep eutectic solvent electrolyte component after optional AgCl colloid compounding. Then, the two components are vortex mixed under heating at about 100° C. The material can be cast from a moderately viscous melt phase into a mold, encapsulating a metal electrode, and set by placing directly into a freezer for a few hours. The freeze-thaw setting process cross-links the hydrogel physically, separating and concentrating polymer from internally formed ice zones and allowing it to partially crystallize. This cross-linking property is important for the robustness of the material, creating tough, rubber-like mechanical properties and resistance to dissolution in contact with various aqueous media.

Aqueous solutions of magnesium chloride (up to 3 M) or lithium chloride (up to 5 M) make up one portion, typically 50% by volume, of the electrolyte solution. Graphene, an electron-conducting 2-dimensional nanomaterial, can be composited at low loading concentrations (~1 wt.) to improve the electrochemical stability of the electrode. Low molecular weight polyvinylpyrrolidone (PVP, 10 kDaltons) is used to stabilize an aqueous dispersion of graphene particles formed under ultrasonication, either from exfoliation of bulk graphite powder starting material or from pre-purified commercial graphene powders. The suspension is then purified by adding equal parts of ethanol and chloroform to break the suspension, centrifuging, and discarding the clear supernatant (which contains excess polymer). The sedimented graphene particles can be further size-selected by centrifugation in pure ethanol if desired, after which they can be resuspended in the aqueous component of the electrolyte solution for addition to the hydrogel. Adding graphene reduces potential drift between pairs of electrodes from about 1 mV/s to about 1 μV/s.

The other component of the electrolyte solution is a skin-safe deep eutectic solvent blend of ethylene glycol and/or propylene glycol and/or urea, with choline chloride in a 2:3 molar ratio. Up to 10 wt % AgCl coarse powder is dispersed into the deep eutectic solvent under heat (e.g., 100 C) and ultrasonication until the solution is transparent, and this is quickly blended with the other half of the polymer powder. Upon cooling, the super-saturated solution precipitates into colloidal particles suspended in the viscous polymer solution.

Rapid setup of electrode contacts can be performed without the use of any elaborate skin preparation, and no pastes, glues, or gels are needed (which may leave uncomfortable residues on the scalp). Instead, a removable superabsorbent sponge cap is applied to the tip of the electrode and wetted with an aqueous electrolyte solution, which is preferably of lower tonicity than the electrode hydrogel formulation, and which preferably contains the same or similar ions. The sponge caps can be fabricated from a polyvinyl alcohol foam or from a foamed hydrogel castable formulation. The caps can be washed and disinfected for reuse, or can be disposable. The sponge cap electrolyte/wetting solution serves as a skin conductivity aid. It preferably contains choline chloride, magnesium chloride, lithium chloride, sodium chloride, and/or potassium chloride, with the optional addition of urea (as skin moisturizer) and skin safe surfactants such as sodium dodecyl sulfate. The sponge cap with wetting agent should be removed shortly after usage and rinsed before the next use, in order to prevent evaporation of solvent.

Figure 3B:
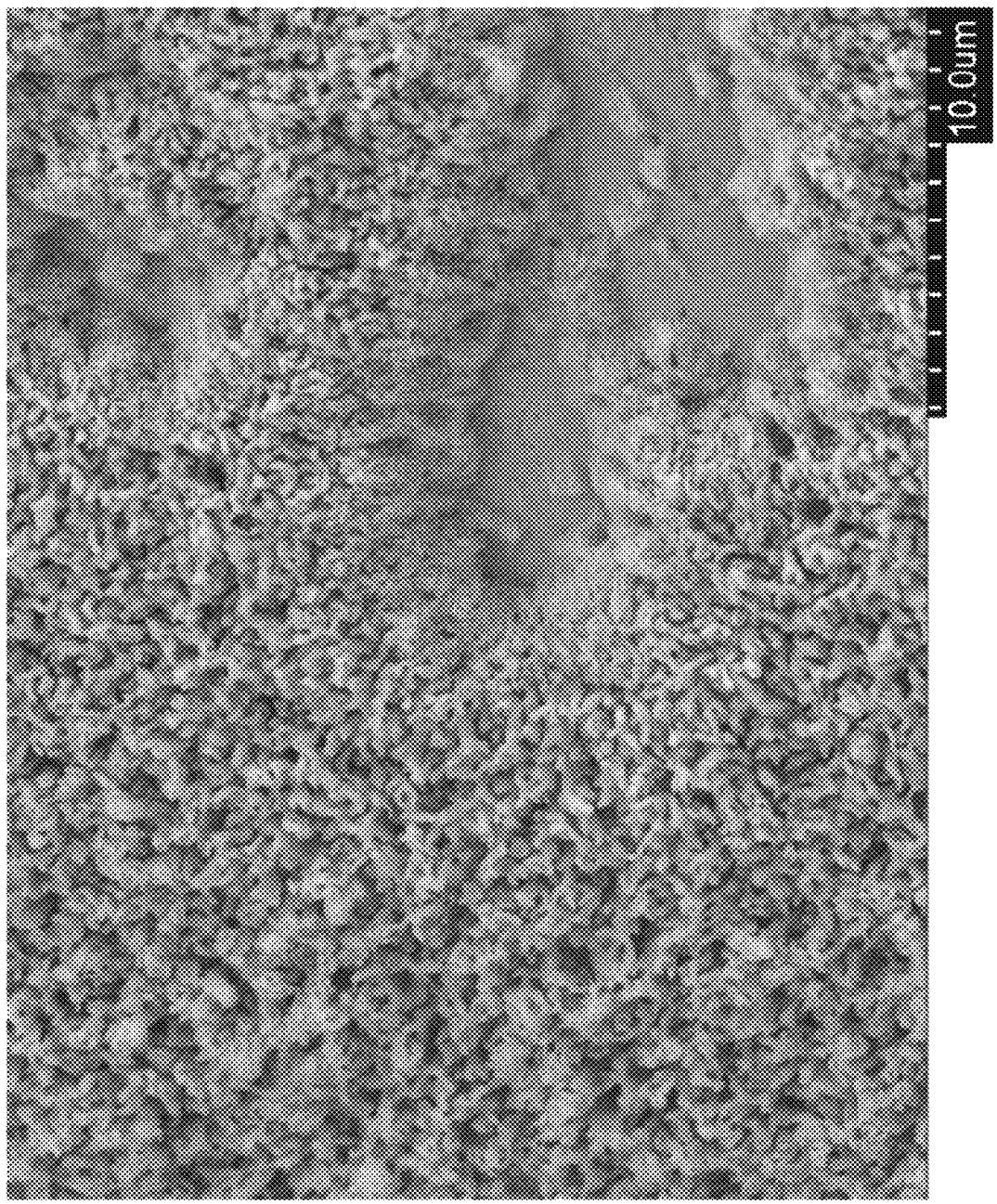

The active sensing surface area of the silver electrode substrate was enhanced using electrochemical modification. The anodization of silver in a chloride containing electrolyte, under some conditions of low current density (<+0.1 mA/cm$^2$), produces a porous layer of silver chloride (AgCl) on the surface of the silver wire. However, the AgCl layer that grows under typical conditions is mechanically weak and may crack off under strain, causing erratic potential fluctuations. If instead one reverses the current, cathodizing the AgCl layer, it reduces back to silver metal. Under some conditions of low current density (<-0.1 mA/cm$^2$), the growth takes place from the metallic substrate layer as reagents diffuse through the pores, and forms dendritic nanostructures that are electrically well-connected, mechanically stable, and have a much higher effective surface area than the original substrate. The nanodendritic structure of the enhanced coating can be seen in FIG. 3B. The AgCl porous layer growth time can be limited to prevent layer rupture (which can be detected as an abrupt drop in reaction voltage under constant current control), typically <30 mins at 0.1 mA/cm$^2$. The subsequent cathodization step should proceed to completion in order to clear any weak AgCl deposit from the outermost portion of the original layer. A final anodization step at <0.1 mA/cm$^2$ may be performed for a much shorter time, typically 5 min, in order to redeposit AgCl material on top of the nanodendritic substrate. This process can be performed in a low concentration hydrochloric acid bath (such as 0.1 M) before the electrode substrate is encapsulated with hydrogel.

Figure 3C:
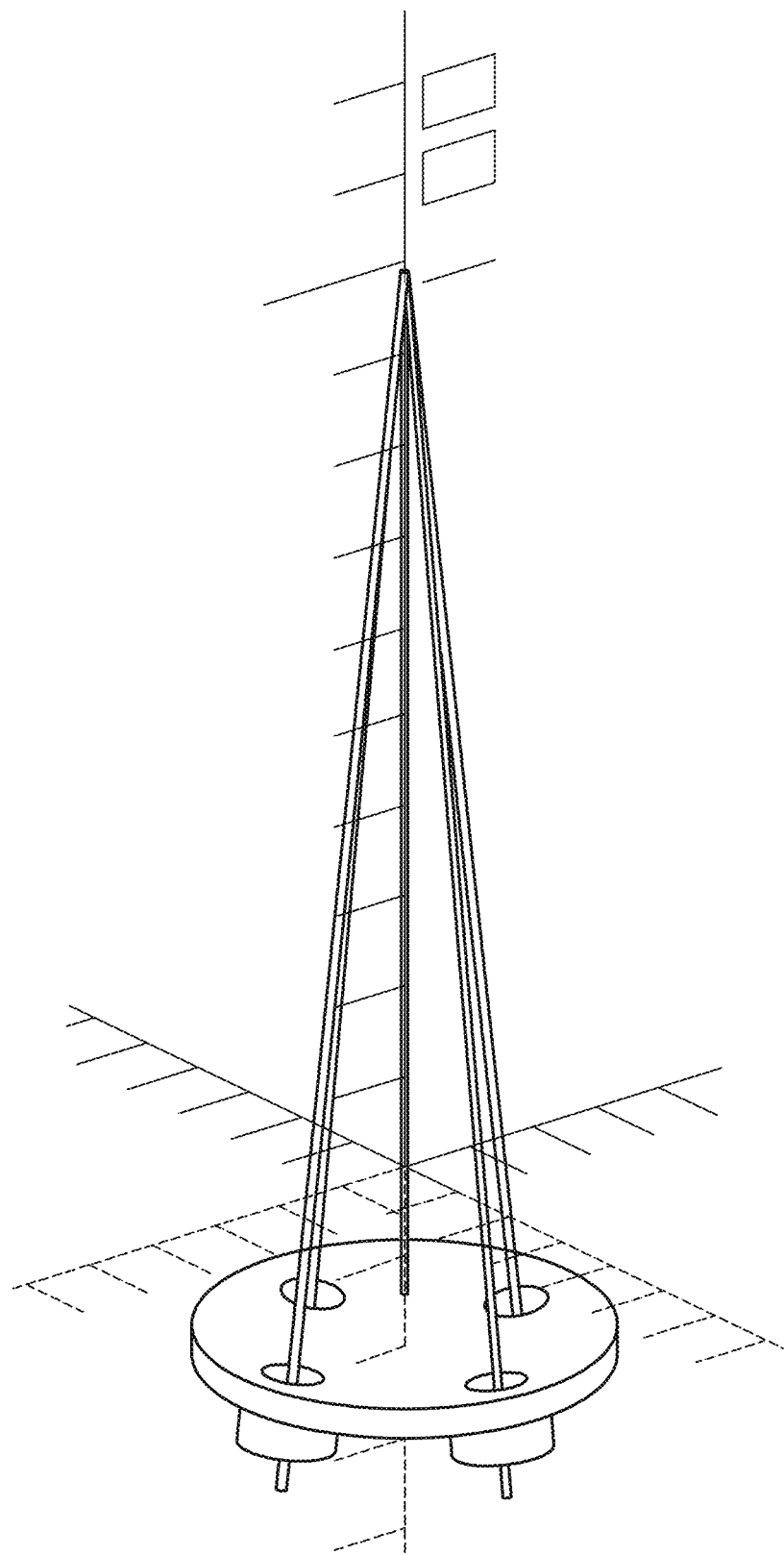

Several electrodes can be inserted into an electrode array, which is required for EFEG measurements. For EFEG, the array assembly has a typical electrode spacing of about 3 cm or less. A support frame for the electrode array is depicted in FIG. 3C. The support frame of the array has guide sockets that are angled so that the tips of the inserted electrodes rest on a sphere of radius 10 cm, which corresponds to an approximation of an average human head. During use, each electrode is inserted into a guide cavity of the support frame and is coupled to a screw plug end of a coaxial cable for attachment to the instrumentation electronics. Snug fitting o-rings can be included on either end of the screw connector to improve hold and block seepage of electrolyte liquids. Prior to use, the electrodes are covered with a removable superabsorbent sponge cap and wetted with a skin conductivity aid electrolyte to achieve high performance measurement with impedances lower than 250 kOhms per channel, typically 50-100 kOhms.

Example 6. Brain-Computer Interface

The brain monitoring device of the present technology can be used in a brain-computer interface, by which a computer user can make selections or activate functions of a computer merely by brain signals. A subject was first cued to look left or right and presented simultaneously with two flashing checker boards, one on the left and one on the right of the screen, for a duration of 5 s. One board flashed at 19 Hz and the other at 23 Hz, and their positions (left, right) were randomly selected. The averaged power spectral density plots (not shown) revealed clearly separable peaks, with EFEG outperforming EEG in peak signal-to-noise ratio (SNR).

Thus, a simple brain-computer interface that classifies a binary decision based on which side the subject is focusing on can be produced using the present device. The classification is to compare the SNRs in 0.5 Hz bands around 19 and 23 Hz. As the decision time decreases, spectral peaks broaden and drop in amplitude, and can fall below the noise floor. This corresponds to a loss of information content, which is why high SNR signals that are more robust to these losses have drastically better performance. In this experiment, the EFEG classification achieved 100% accuracy in 2 s of data collection, significantly outperforming the EEG classification. The EFEG classification also achieved a maximum information transfer rate of 30 bits/min which is among the highest values reported.

Example 7. Diagnosis of Amblyopia

Figure 8A:
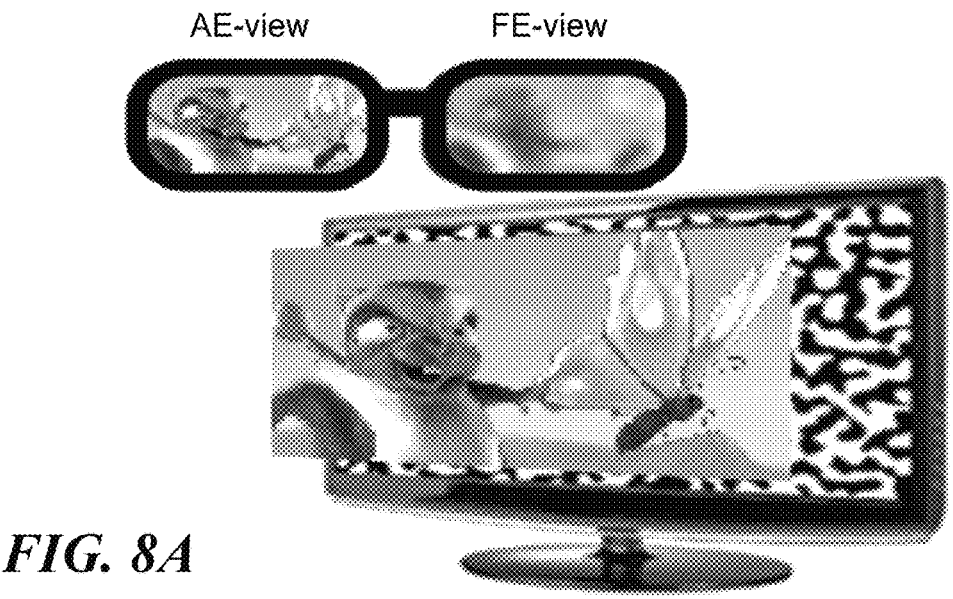
FIGS. 8A and 8B show tVEP responses for an amblyotropic subject comparing the affected and normal eyes.
Figure 8B:
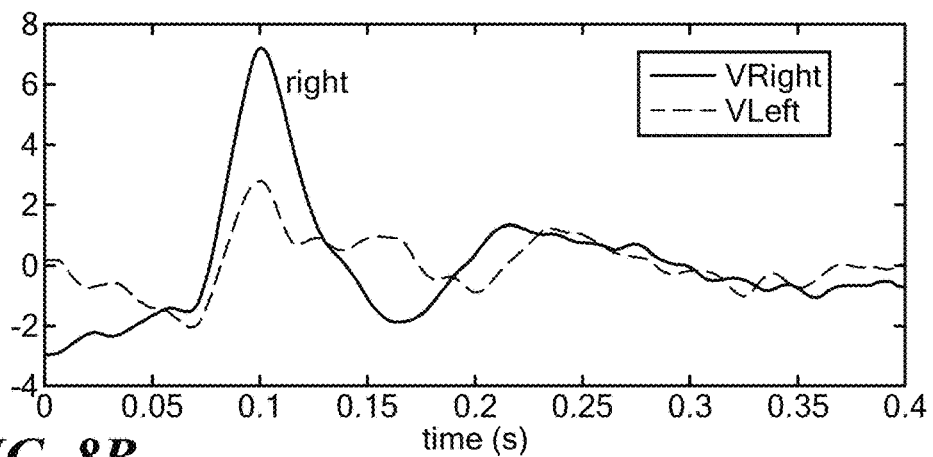
Figure 8C:
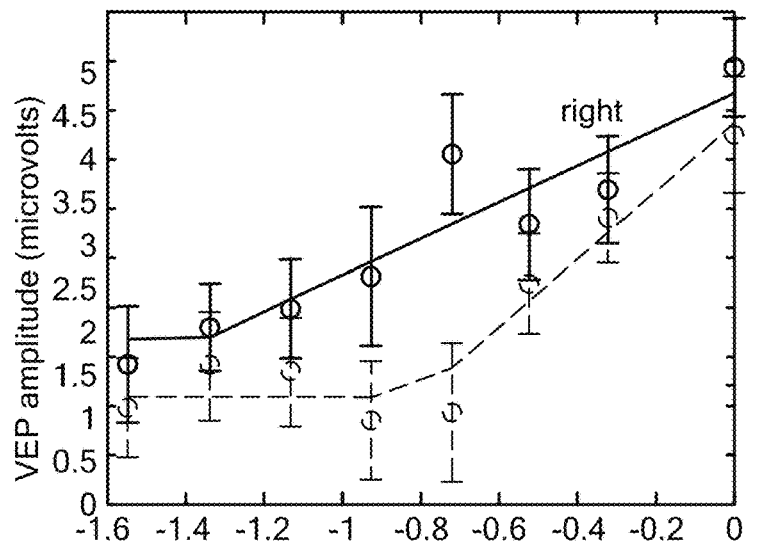

Diagnosis of a subject with amblyopia was tested using a virtual reality movie in which the amblyopic eye was shown a clear image and the other eye was shown an unfocused image. A representation of the dichoptic presentation by the theranostic brain and vision monitoring device of the present technology is shown in FIG. 8A. During the movie, tVEP data were acquired using a theranostic device according to the present technology, and the results are shown in FIGS. 8B and 8C. The amblyopic left eye showed a greatly decreased P100 amplitude (FIG. 8B) and stronger contrast sensitivity compared to the normal right eye.

Example 8. Diagnosis of Glaucoma

Figure 9A:
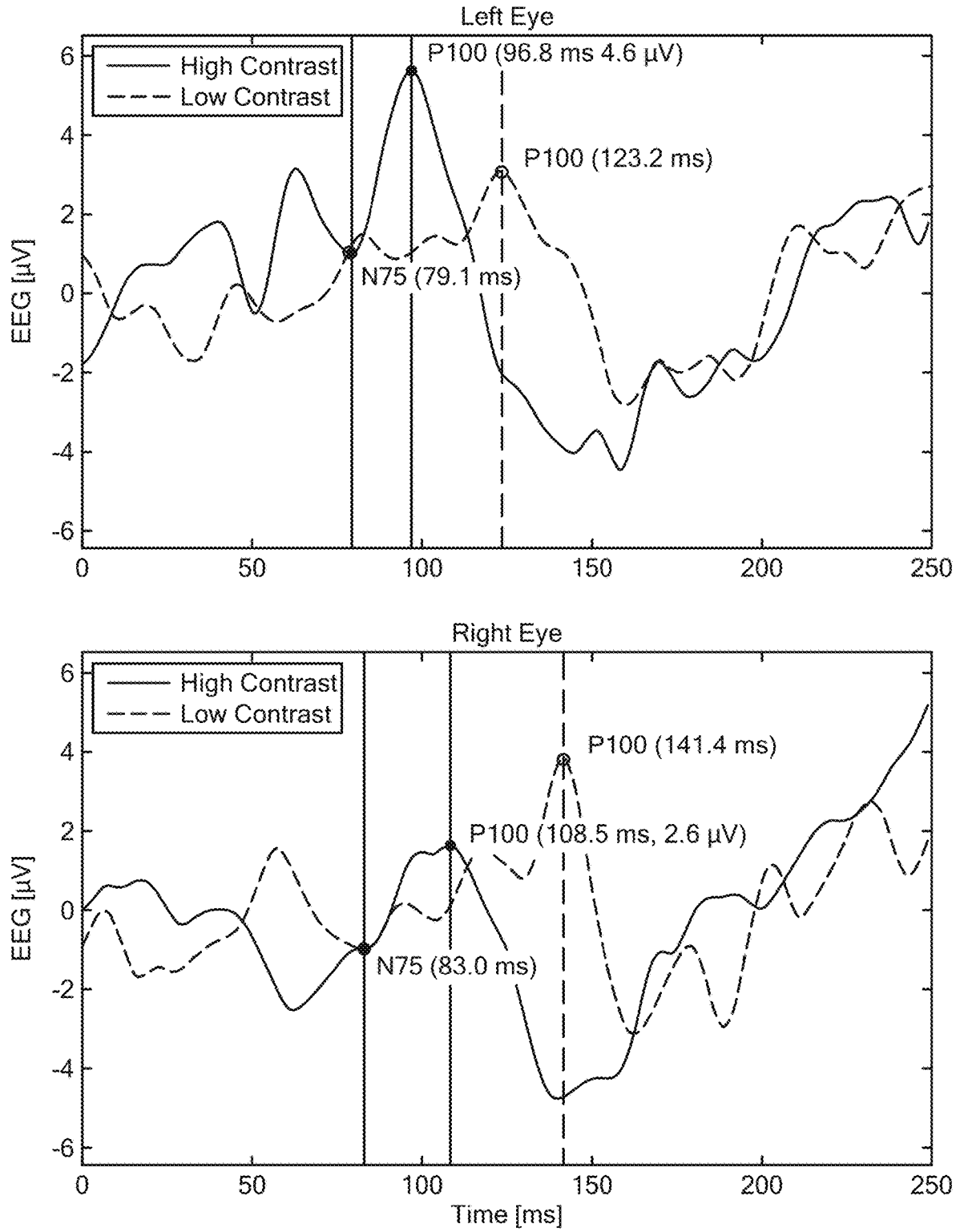
FIGS. 9A and 9B show tVEP responses for a subject diagnosed with early stage glaucoma in one eye.
Figure 9B:
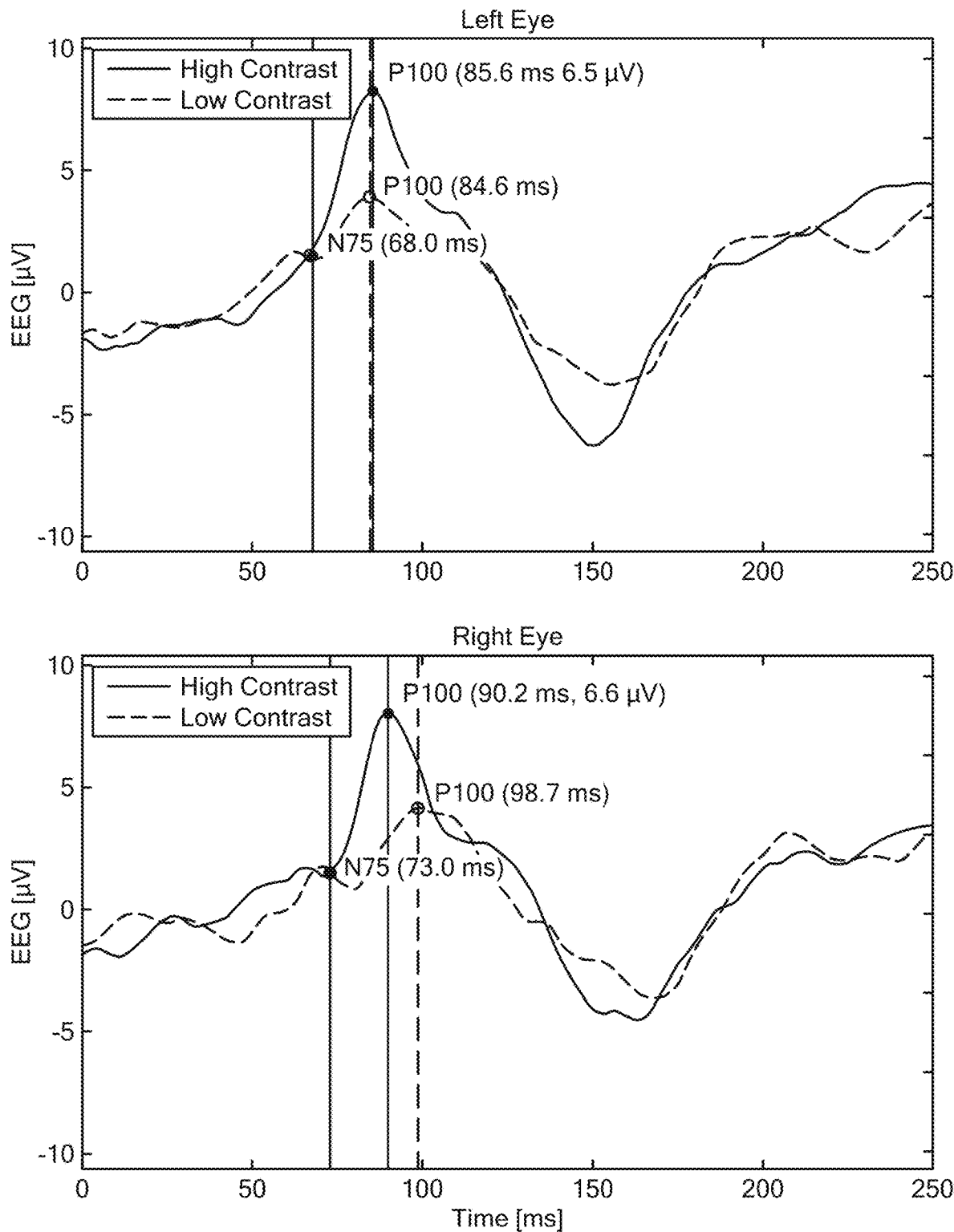

The theranostic brain and vision monitoring device of the present technology enables convenient diagnostic measurement of glaucoma at early stages by detecting vision loss. FIG. 9A shows the strong contrast sensitivity and large shift of the P100 from 100 ms to 141 ms, compared with the tVEP for a normal subject tVEP for a subject diagnosed with early glaucoma in the right eye. The signals show strong contrast sensitivity and latency of the P100 peak. FIG. 9B shows tVEP for a normal subject.

Figure 10A:
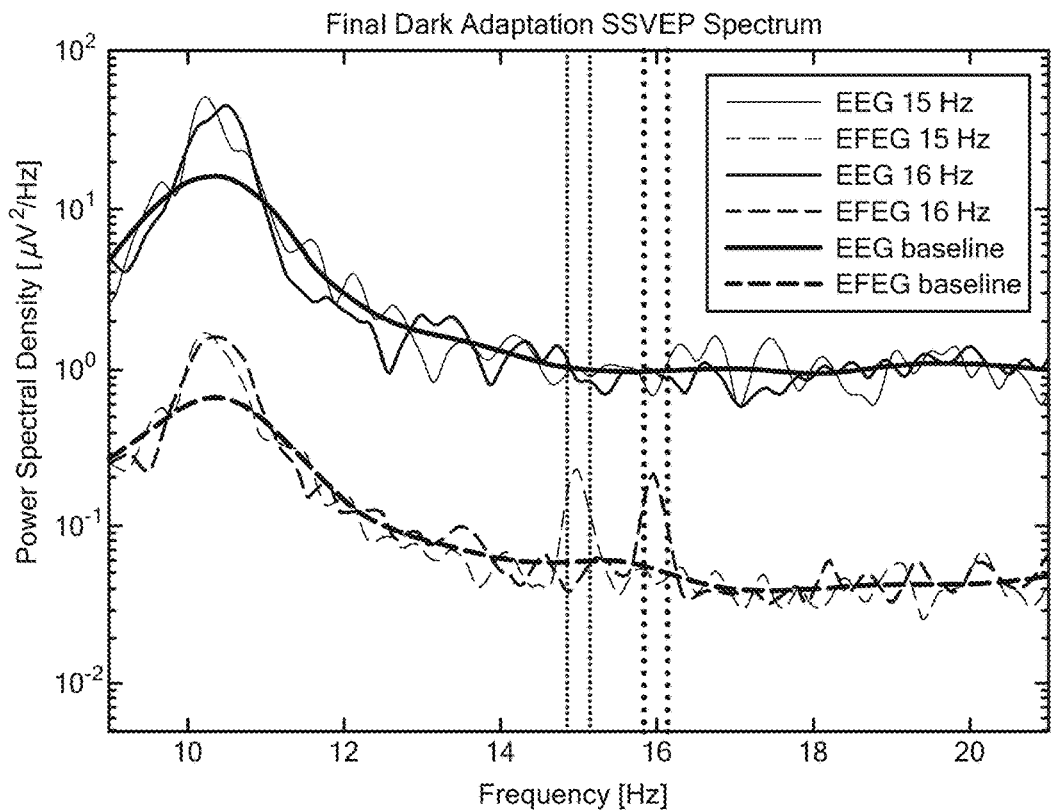
FIGS. 10A-10C show ssVEPF signals in dark adaptation VEPF mode as power density spectrum (10A), SNR (10B), and SNR as a function of recovery from a bleaching flash (10C).
Figure 10B:
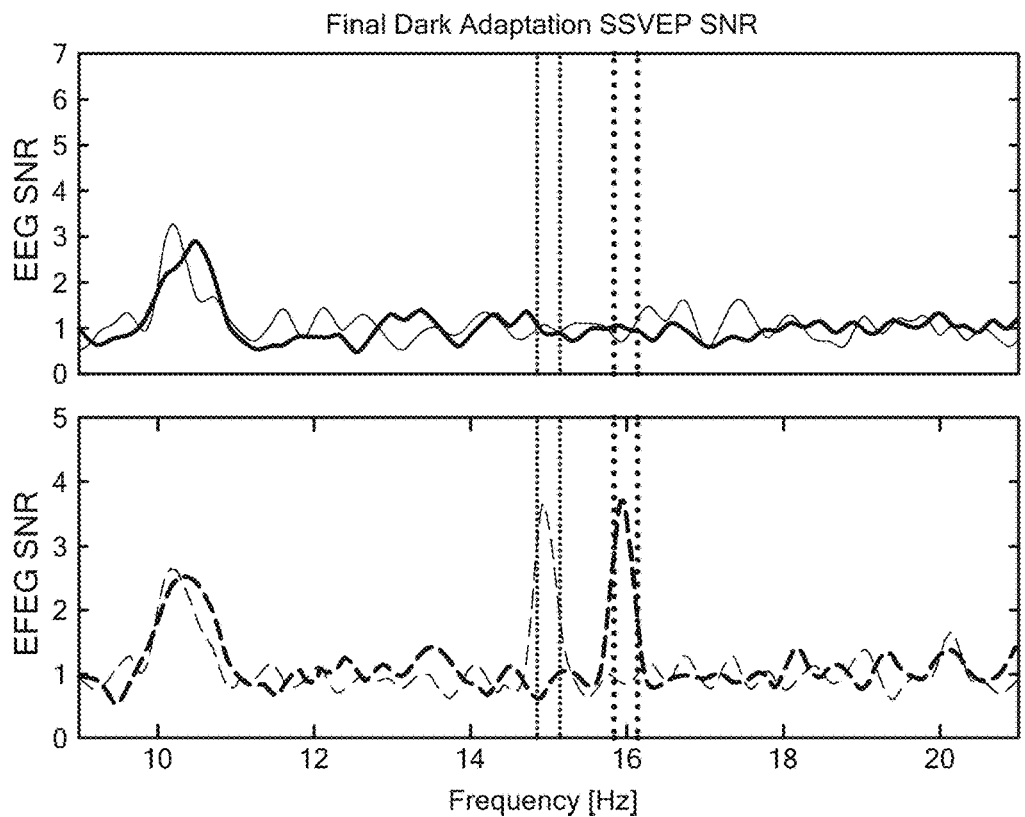
Figure 10C:
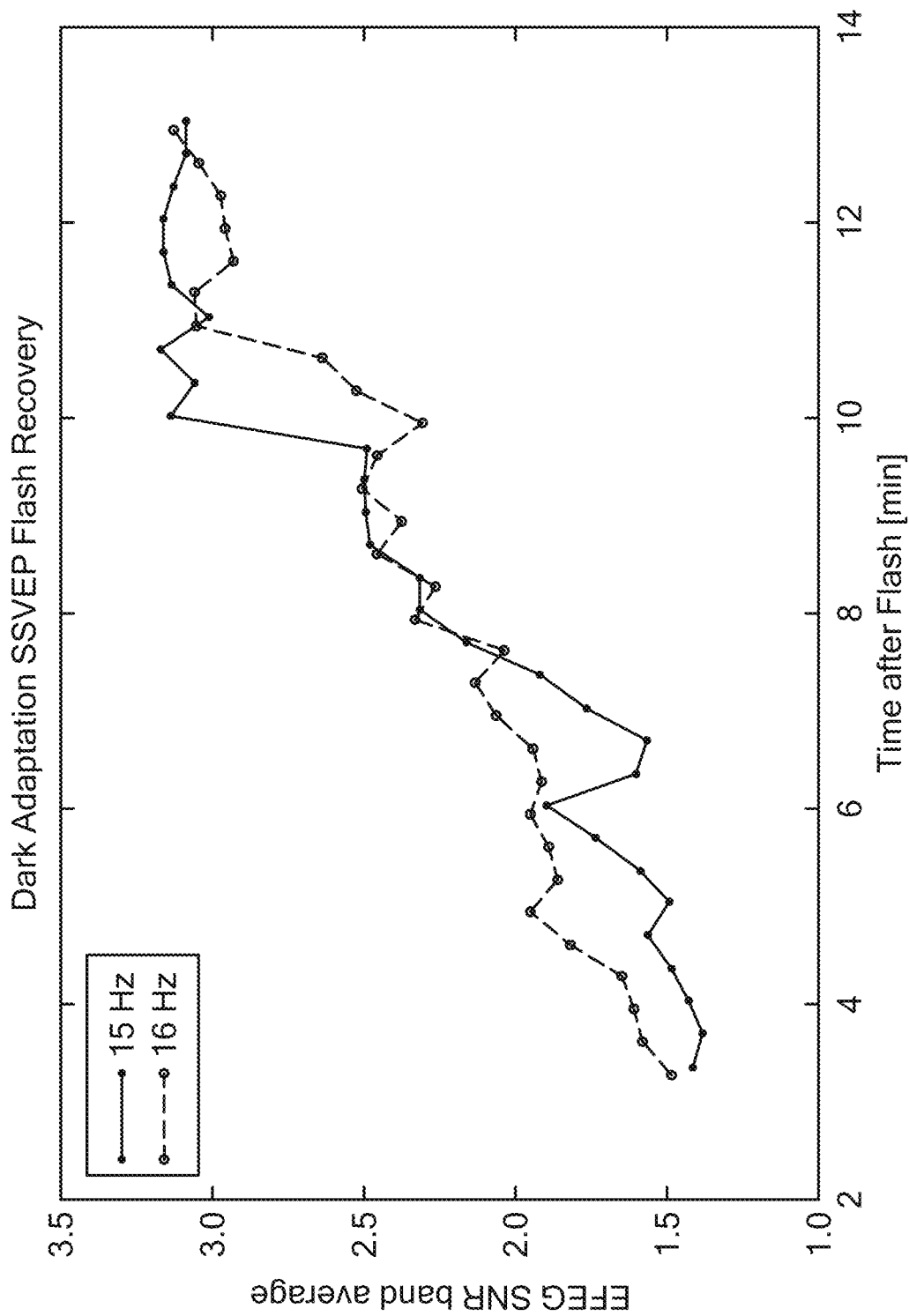

Example 9. Dark Adaptation Recovery for Diagnosis of Concussion or Age-Related Macular Degeneration The theranostic brain and vision monitoring device of the present technology was configured in the dark adaptation VEPF (DA-VEPF) mode to measure VEPF recovery under dark adaptation. FIGS. 10A-10C show typical ssVEPF signals from a normal subject. FIG. 10A shows the power density spectrum, FIG. 10B shows SNR, and FIG. 10C shows SNR during recovery from a photobleaching flash. It is apparent that the EFEG mode was superior in sensitivity to the EEG mode for these measurements. The DA-VEPF mode is particularly suited for diagnosis of Photosensitivity following Concussion and retinal metabolism delays in Age-related Macular Degeneration.

As used herein, "consisting essentially of" allows the inclusion of materials or steps that do not materially affect the basic and novel characteristics of the claim. Any recitation herein of the term "comprising", particularly in a description of components of a composition or in a description of elements of a device, can be exchanged with "consisting essentially of" or "consisting of".

While the present invention has been described in conjunction with certain preferred embodiments, one of ordinary skill, after reading the foregoing specification, will be able to effect various changes, substitutions of equivalents, and other alterations to the compositions and methods set forth herein.

REFERENCES

[1] Chi Y M, Wang Y T, Wang Y, Maier C, Jung T P, Cauwenberghs G 2012 Dry and noncontact EEG sensors for mobile brain-computer interfaces IEEE Trans Neural Syst Rehabil Eng. 20(2) 228-35
[2] Chi Y M, Jung T P, and Cauwenberghs G 2010 Dry-Contact and Noncontact Biopotential Electrodes: Methodological Review IEEE Reviews in Biomedical Engineering 3 106-119
[3] Oha S, Kumara P S, Kwona H, Varadan V K 2012 Wireless Brain-Machine Interface Using EEG and EOG: Brain Wave Classification and Robot Control Nanosensors, Biosensors, and Info-Tech Sensors and Systems in Varadan V K (Ed.): Proc. of SPIE 8344, 83440U
[4] Morikawa K, Matsumoto A, Patki S, Grundlehner B, Verwegen A, Xu J, Mitra S and Penders J 2013 Compact Wireless EEG System with Active Electrodes for Daily Healthcare Monitoring IEEE Int Conf on Consumer Electronics (ICCE) 2013 204-205
[5] Lin C T, Ko L W, Chang C J, Wang Y T, Chung C H, Yang F S, Duann J R, Jung T P, and Chiou J C 2009 Wearable and Wireless Brain-Computer Interface and Its Applications Augmented Cognition (HCII 2009, LNAI 5638) ed Schmorrow D D et al pp 741-748
[6] Hoyeoul P, Boram M, Sun K Y 2013 Power consumption of wireless EEG device for BCI application Portable EEG system for BCI International Winter Workshop on Brain-Computer Interface (BCI) (2013) pp 100-102
[7] Filipe S, Charvet G, Foerster M, Porcherot J, Bêche J F, Bonnet S, Audebert P, Regis G, Zongo B, Robinet S, Condemine C, Mestais C, Guillemaud R 2011 A wireless multichannel EEG recording platform Proc. 33rd Annual International Conference of the IEEE EMBS pp 6319-6322
[8] Petrov Y, Sridhar S 2013 Electric Field Encephalography as a Tool for Functional Brain Research: A Modeling Study PLOSOne v.8 e67692
[9] Sridhar S, Yavuzcetin O, and Petrov Y 2012 Electric field encephalography: Electric Field based brain signal detection and monitoring USPTO PCT/US2012/050184, WO2014025353 A1 (August 2012)
[10] Petrov Y, Nador J, Hughes C, Tran S, Yavuzcetin O, and Sridhar S 2014 Ultra-dense EEG Sampling Shows Twofold Increase of Functional Brain Information NeuroImage 90 140-5 (doi: 10.1016/j.neuroimage.2013.12.041)
[11] Sridhar S, Yavuzcetin O, Petrov Y and Chowdhury K 2014 Sensor System And Process For Measuring Electric Activity Of The Brain, Including Electric Field Encephalography PCT Application No. PCT/US2014/043425 (June 2014)
[12] Bullock T H, Hopkins C D, Popper A N and Fay R R 2005 Electroreception, Springer Press
[13] Fields R 2007 The shark's electric sense Scientific American Magazine 297(2) 74-81
[14] Scheer H, Sander T and Trahms L 2006 The influence of amplifier, interface, and biological noise on signal quality in high-resolution EEG recordings Physiol. Meas. 27 109-117
[15] Petrov Y 2012 Anisotropic spherical head model and its application to imaging electric activity of the brain Physical Review E 86(1) 011917
[16] Grummett T S, Leibbrandt R E, Lewis T W, DeLosAngeles D, Powers D M, Willoughby J O, Pope K J, Fitzgibbon S P 2015 Measurement of neural signals from inexpensive, wireless and dry EEG systems Physiol. Meas. 36(7) 1469-84
[17] Tallgren P, Vanhatalo S, Kaila K, Voipio J 2005 Evaluation of commercially available electrodes and gels for recording of slow EEG potentials Clinical Neurophysiology 116 799-806
[18] Reagor M K, Zong C, Jafari R 2014 Maximizing Information Transfer Rates in an SSVEP-based BCI using Individualized Bayesian Probability Measures Proc. 36th Annual International Conference of the IEEE EMBS pp 654-657 (doi 10.1109/EMBC.2014.6943676)
[19] Johansson B I, Jakobsson P, Fourier-analysed steady-state VEPs in pre-school children with and without normal binocularity. Doc Ophthalmol 112(1):13-22 (2006) PMID 16633721
[20] Lew, Henry L., Poole, John H., Castaneda, Annabel, Salerno, Rose Marie, Gray, Max B S Prognostic Value of Evoked and Event-related Potentials in Moderate to Severe Brain Injury, Journal of Head Trauma Rehabilitation, July/August 2006, Volume:21 Number 4, page 350-360
[21] Prata T S, Lima V C, De Moraes C G, Trubnik V, Derr P, Liebmann J M, Ritch R, Tello C., Short Duration Transient Visual Evoked Potentials in Glaucomatous Eyes. J Glaucoma. 2011 May 10

What is claimed is:

1. A brain sensing theranostic headset device comprising:
a sensor unit comprising an array of electrodes configured for providing electrical contact between the electrodes and the scalp of a subject wearing the device, wherein the electrodes are configured for recording brain signals in an electric field encephalography (EFEG) mode;
a headband upon which the sensor unit is mounted, the headband wearable on the subject's head and adapted for positioning the sensor unit adjacent to a selected brain region;
a display unit comprising a display capable of displaying visual stimuli to one or both eyes of the subject; and
an event triggering system comprising:
a digital event trigger configured to generate an optical signal in a selected region of the display signaling a beginning and/or a type of a visual stimulus; and
an optical sensor covering said selected region of the display and configured to receive the optical signal generated by the digital event trigger;
wherein the device is capable of measuring signals from the brain of the subject in response to the visual stimuli, wherein the signals include transient and/or steady state visual evoked potentials and fields (VEPF).

2. The device of claim 1, further comprising an amplifier module, signal processing module, and wireless transmitter, each located on a separate circuit board within the sensor unit.

3. The device of claim 1, wherein the electrode array comprises a reference electrode and an array of sensing electrodes surrounding the reference electrode.

4. The device of claim 1, wherein the selected brain region is the visual cortex, and the device is capable of recording the transient and/or steady state visual evoked potentials and fields from the visual cortex of the subject in response to the visual stimuli delivered through the display unit.

5. The device of claim 1, wherein the display unit comprises a mobile device and a mounting structure for the mobile device, the mounting structure attached to the headband, and wherein the mobile device displays the visual stimuli.

6. The device of claim 1, wherein the display unit comprises virtual reality goggles or an augmented reality system.

7. The device of claim 1, wherein the display unit comprises a video screen of a device not attached to the headband.

8. The device of claim 1, wherein the display unit is capable of monocular, dichoptic, stereoscopic, binocular, hemifield, multi-focal, static, dynamic, or chromatic image presentation to the subject.

9. The device of claim 1, wherein the device is portable, self-contained, and capable of setup and obtaining data from a human subject in less than about one minute.

10. A method of evaluating brain function or vision of a subject, the method comprising:
   (a) mounting the brain sensing theranostic headset device of claim 1 on the head of the subject, whereby the display unit is oriented to display the visual stimuli to the eyes of the subject and the electrodes of the sensor unit are in contact with the subject's scalp disposed over a selected brain region;
   (b) displaying one or more said visual stimuli to one or both eyes of the subject using the headset device;
   (c) measuring signals from the selected brain region of the subject in response to the one or more visual stimuli; and
   (d) evaluating the subject's brain function or vision based on the measured signals.

11. The device of claim 1, wherein the event triggering system comprises a plurality of optical sensors, each covering a different selected region of the display, the plurality of selected regions of the display configured to provide a combined digital optical signal that identifies one or more characteristics of the visual stimulus.

12. A brain sensing theranostic headset device comprising:
   a sensor unit comprising an array of electrodes configured for providing electrical contact between the electrodes and the scalp of a subject wearing the device, wherein the sensor unit comprises a plurality of electrodes capable of forming a contact impedance of less than 200 kohms with the scalp of a subject wearing the device, and wherein the electrodes are configured for recording brain signals in an electric field encephalography (EFEG) mode;
   a headband upon which the sensor unit is mounted, the headband wearable on the subject's head and adapted for positioning the sensor unit adjacent to a selected brain region;
   a display unit comprising a display capable of displaying visual stimuli to one or both eyes of the subject; and
   an event triggering system comprising:
      a digital event trigger configured to generate an optical signal in a selected region of the display signaling a beginning and/or a type of a visual stimulus; and
      an optical sensor covering said selected region of the display and configured to receive the optical signal generated by the digital event trigger;
   wherein the device is capable of essentially simultaneous display of visual stimuli to the subject and acquisition of brain signals from the subject with a latency of about 1 millisecond or less.

13. The device of claim 12, wherein the latency is about 1 microsecond or less.

14. The device of claim 12, wherein the display unit comprises a phototransistor coupled to a high gain current-voltage amplifier that provides a digital signal used to trigger data acquisition after presentation of a visual stimulus.

15. The device of claim 12 further comprising a control unit, wherein acquired data are time stamped using only one clock or a set of clocks synchronized using Network Time Protocol and compensated to a relative drift of less than 1 millisecond per hour, and wherein the clocks are disposed either in the control unit or in the display unit.

16. The device of claim 12, wherein a mobile device serves as both the display unit and a control unit.

17. The device of claim 12, wherein the display unit comprises a mobile device and a mounting structure for the mobile device, the mounting structure attached to the headband, and wherein the mobile device displays the visual stimuli.

18. The device of claim 12, wherein the display unit is capable of dichoptic, binocular, or monocular image presentation to the subject.

19. The device of claim 12, wherein the device is portable, self-contained, and capable of setup and obtaining data from a human subject in less than one minute.

20. The device of claim 12, wherein the event triggering system comprises a plurality of optical sensors, each covering a different selected region of the display, the plurality of selected regions of the display configured to provide a combined digital optical signal that identifies one or more characteristics of the visual stimulus.

21. A method of evaluating brain function or vision of a subject, the method comprising the steps of:
   (a) providing the device of claim 12;
   (b) displaying one or more visual stimuli to the subject using said device; and
   (c) measuring from the subject's brain an EFEG signal in the form of a transient visual evoked potential or stimulus (tVEPF) or a steady state visual evoked potential or stimulus (ssVEPF) using said device.

* * * * *